(12) United States Patent
Bazard et al.

(10) Patent No.: US 9,937,359 B1
(45) Date of Patent: Apr. 10, 2018

(54) PLASMONIC STIMULATION OF ELECTRICALLY EXCITABLE BIOLOGICAL CELLS

(71) Applicants: Parveen Bazard, Tampa, FL (US); Robert Dana Frisina, Tampa, FL (US); Joseph Paul Walton, Tampa, FL (US); Venkat Rama Bhethanabotla, Tampa, FL (US)

(72) Inventors: Parveen Bazard, Tampa, FL (US); Robert Dana Frisina, Tampa, FL (US); Joseph Paul Walton, Tampa, FL (US); Venkat Rama Bhethanabotla, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/048,756

(22) Filed: Feb. 19, 2016

Related U.S. Application Data

(60) Provisional application No. 62/118,103, filed on Feb. 19, 2015.

(51) Int. Cl.
*A61N 5/06* (2006.01)
*A61N 5/067* (2006.01)

(52) U.S. Cl.
CPC ......... *A61N 5/0622* (2013.01); *A61N 5/0603* (2013.01); *A61N 2005/063* (2013.01); *A61N 2005/0605* (2013.01); *A61N 2005/067* (2013.01); *A61N 2005/0663* (2013.01)

(58) Field of Classification Search
CPC ............... A61N 5/0622; A61N 5/0603; A61N 2005/0605; A61N 2005/063; A61N 2005/0663; A61N 2005/067
USPC .................................................... 607/88–93
See application file for complete search history.

(56) References Cited

U.S. PATENT DOCUMENTS

| 7,798,164 B2 | 9/2010 | Adleman et al. |
| 8,409,263 B2 | 4/2013 | Peyman |
| 8,475,506 B1 | 7/2013 | Bendett et al. |
| 8,493,560 B2 | 7/2013 | Shopova et al. |

(Continued)

OTHER PUBLICATIONS

Lugo et al, Remote switching of cellular activity and cell signaling using light in conjunction with quantum dots; Biomedical Optics Express; Published Feb. 8, 2012; doi: 10.1364/BOE.3.000447.*

(Continued)

*Primary Examiner* — Gary Jackson
*Assistant Examiner* — Jonathan Kuo
(74) *Attorney, Agent, or Firm* — Thomas | Horstemeyer, LLP

(57) ABSTRACT

A novel method to stimulate electrically active biological cells using visible wavelength light and metallic nanoparticles possessing plasmonic properties is presented herein. Using this technology, prosthetic devices such as cochlear and retinal implants and cardiac pacemakers can be developed to have superior properties as compared to the currently utilized electrical stimulation designs. These properties include improved spatial resolution; less or non-invasive devices; and higher fidelity of transduction. An additional advantage of using visible light wavelengths is the avoidance of unwanted heating of surrounding tissue that occurs with infrared stimulation.

20 Claims, 22 Drawing Sheets

(56) References Cited

U.S. PATENT DOCUMENTS

| | | | |
|---|---|---|---|
| 2009/0326614 A1* | 12/2009 | El-Sayed | A61K 41/0052 607/88 |
| 2010/0003316 A1 | 1/2010 | Vo Dinh et al. | |
| 2012/0034622 A1* | 2/2012 | Ignatius | B82Y 5/00 435/7.2 |
| 2012/0263793 A1 | 10/2012 | Vitaliano | |
| 2012/0271293 A1* | 10/2012 | Abrams | A61F 2/82 606/28 |
| 2013/0059316 A1 | 3/2013 | Geddes | |
| 2015/0283398 A1* | 10/2015 | Andersen | A61K 38/168 607/88 |

OTHER PUBLICATIONS

Bazard P, Frisina RD, Walton JP, Bhethanabotla VR. Nanoparticle-based Plasmonic Transduction for Modulation of Electrically Excitable Cells. Scientific Reports. 2017;7:7803. doi:10.1038/s41598-017-08141-4.*

Weils, J., Kao, C., Jansen, E. D., Konrad, P., and Mahadevan-Jansen, A. (2005). Application of infrared light for in vivo neural stimulation. Journal of Biomedical Optics, 10(6):064003-064003-12.

Wells, J., Kao, C., Konrad, P., Milner, T., Kim, J., Mahadevan-Jansen, A., and Jansen, E. D. (2007). Biophysical mechanisms of transient optical stimulation of peripheral nerve. Biophysical Journal, 93(7):2567-2580.

Shapiro, M. G., Homma, K., Villarreal, S., Richter, C.-P., and Bezanilla, F. (2012). Infrared light excites cells by changing their electrical capacitance. Nature Communications, 3:736.

Izzo, A. D., Richter, C.-P., Jansen, E. D., and Walsh, J. T. (2006). Laser stimulation of the auditory nerve. Lasers in Surgery and Medicine, 38(8):745-753.

Izzo, A. D., Walsh, J. T., Jansen, E. D., Bendett, M., Webb, J., Ralph, H., and Richter, C.-P. (2007b). Optical parameter variability in laser nerve stimulation: a study of pulse duration, repetition rate, and wavelength. Biomedical Engineering, IEEE Transactions on, 54(6):1108-1114.

Littlefield, P. D., Vujanovic, I., Mundi, J., Matic, A. I., and Richter, C.-P. (2010). Laser stimulation of single auditory nerve fibers. The Laryngoscope, 120(10):2071-2082.

Rajguru, S. M., Matic, A. I., Robinson, A. M., Fishman, A. J., Moreno, L. E., Bradley, A., Vujanovic, I., Breen, J., Wells, J. D., Bendett, M., et al. (2010). Optical cochlear implants: evaluation of surgical approach and laser parameters in cats. Hearing Research, 269(1):102-111.

Shipway, A. N., Katz, E., and Willner, I. (2000). Nanoparticle arrays on surfaces for electronic, optical, and sensor applications. ChemPhysChem, 1(1):18-52.

Daniel, M.-C. and Astruc, D. (2004). Gold nanoparticles: assembly, supramolecular chemistry, quantum-size-related properties, and applications toward biology, catalysis, and nanotechnology. Chemical Reviews, 104(1):293-346.

Otsuka, H., Nagasaki, Y., and Kataoka, K. (2003). Pegylated nanoparticles for biological and pharmaceutical applications. Advanced Drug Delivery Reviews, 55(3):403-419.

Salata, O. V. (2004). Applications of nanoparticles in biology and medicine. Journal of Nanobiotechnology, 2(1):3.

Kruis, F. E., Fissan, H., and Peled, A. (1998). Synthesis of nanoparticles in the gas phase for electronic, optical and magnetic applications a review. Journal of Aerosol Science, 29(5):511-535.

Coronado, E A., Encina, E. R., and Stefani, F. D. (2011). Optical properties of metallic nanoparticles: manipulating light, heat and forces at the nanoscale. Nanoscale, 3:4042-4059.

Huang, X. and El-Sayed, M. A. (2010). Gold nanoparticles: optical properties and implementations in cancer diagnosis and photothermal therapy. Journal of Advanced Research, 1(1):13-28.

Lowe, L. B., Brewer, S. H., Krmer, S., Fuierer, R. R., Qian, G., Agbasi-Porter, C. O., Moses, S., Franzen, S., and Feldheim, D. L (2003). Laser-induced temperature jump electrochemistry on gold nanoparticle-coated electrodes. Journal of the American Chemical Society, 125(47):14258-14259.

Yao, J. Liu, B. and Qin, F. (2009). Rapid temperature jump by infrared diode laser irradiation for patch-clamp studies. Biophysical Journal, 96(9):3611-3619.

Yoo, S., Hong S., Choi, Y., Park, J.-H., and Nam, Y. (2014). Photothermal inhibition of neural activity with near-infrared-sensitive nanotransducers. ACS Nano, 8(8):8040-8049.

Eom, K., Kim, J., Choi, J. M., Kang, T., Chang, J. W., Byun, K. M., Jun, S. B., and Kim, S. J. (2014). Enhanced infrared neural stimulation using localized surface plasmon resonance of gold nanorods. Small, 10(19):3853-3857.

Duke, A. R., Jenkins, M. W., Lu, H., McManus, J. M., Chiel, H. J., and Jansen, E. D. (2013). Transient and selective suppression of neural activity with infrared light. Scientific reports, 3.

Kang, J. X., Xiao, Y. F., and Leaf, A. (1995). Free, long-chain, polyunsaturated fatty acids reduce membrane electrical excitability in neonatal rat cardiac myocytes. Proceedings of the National Academy of Sciences, 92(9):3997-4001.

Johansson, S. (1994). Graded action potentials generated by differentiated human neuroblastoma cells. Acta Physiologica Scandinavica, 151(3):331-341.

Tosetti, P., Taglietti, V., and Toselli, M. (1998). Functional changes in potassium conductances of the human neuroblastoma cell line sh-sy5y during in vitro differentiation. Journal of Neurophysiology, 79(2):648-658.

Urban, Alexander S. et al. 'Controlled Nanometric Phase Transitions on Phospholipid Membranes Using Plasmonic Heating of Single Gold Nanoparticles'. Biophysical Journal 98.3 (2010): 2903-2908.

Yuan, Hsiangkuo et al. 'In Vivo Particle Tracking and Photothermal Ablation Using Plasmon-Resonant Gold Nanostars'. Nanomedicine: Nanotechnology, Biology and Medicine 8.8 (2012): 1355-1363.

Kabashin, A. V. et al. 'Plasmonic Nanorod Metamaterials for Biosensing'. Nat Mater 8.11 (2009): 867-871.

* cited by examiner

- SPR = Metal Nanoparticles + Visible
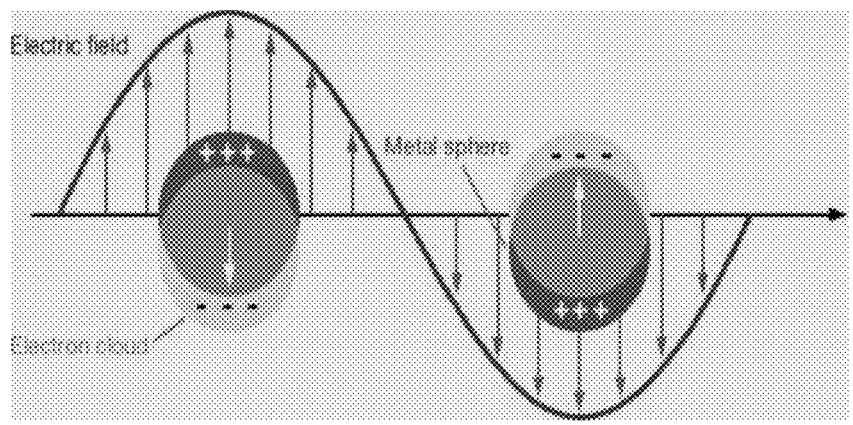
- Plasmonic Heating
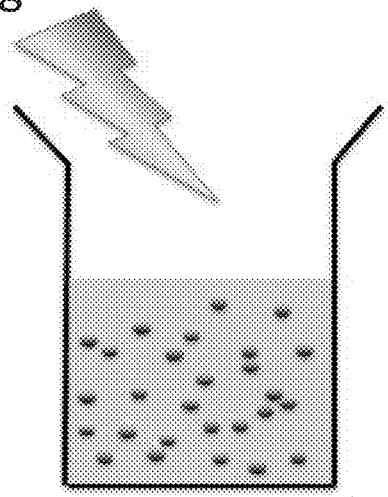
*FIG. 1*

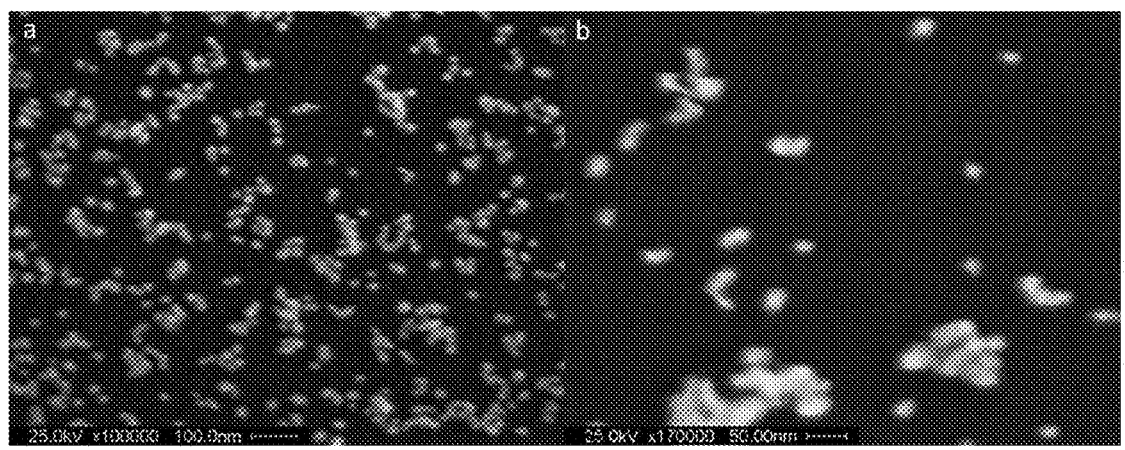
*FIG. 7A-B*
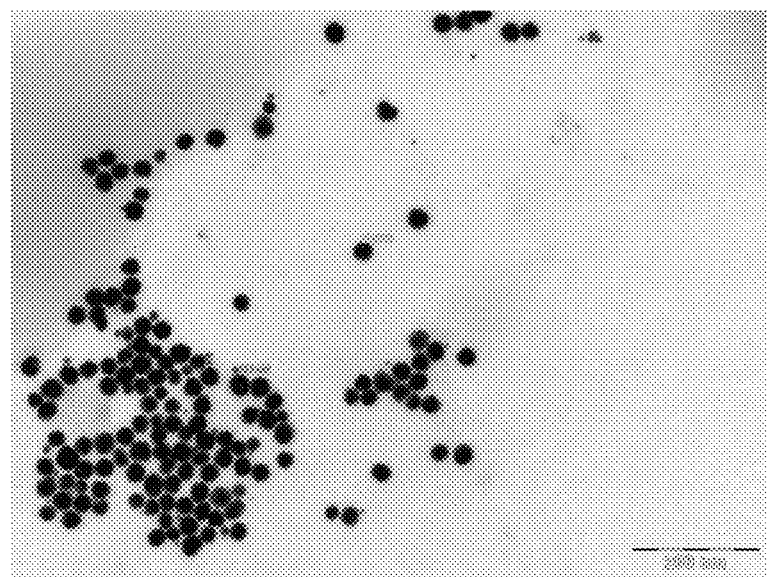
*FIG. 8*

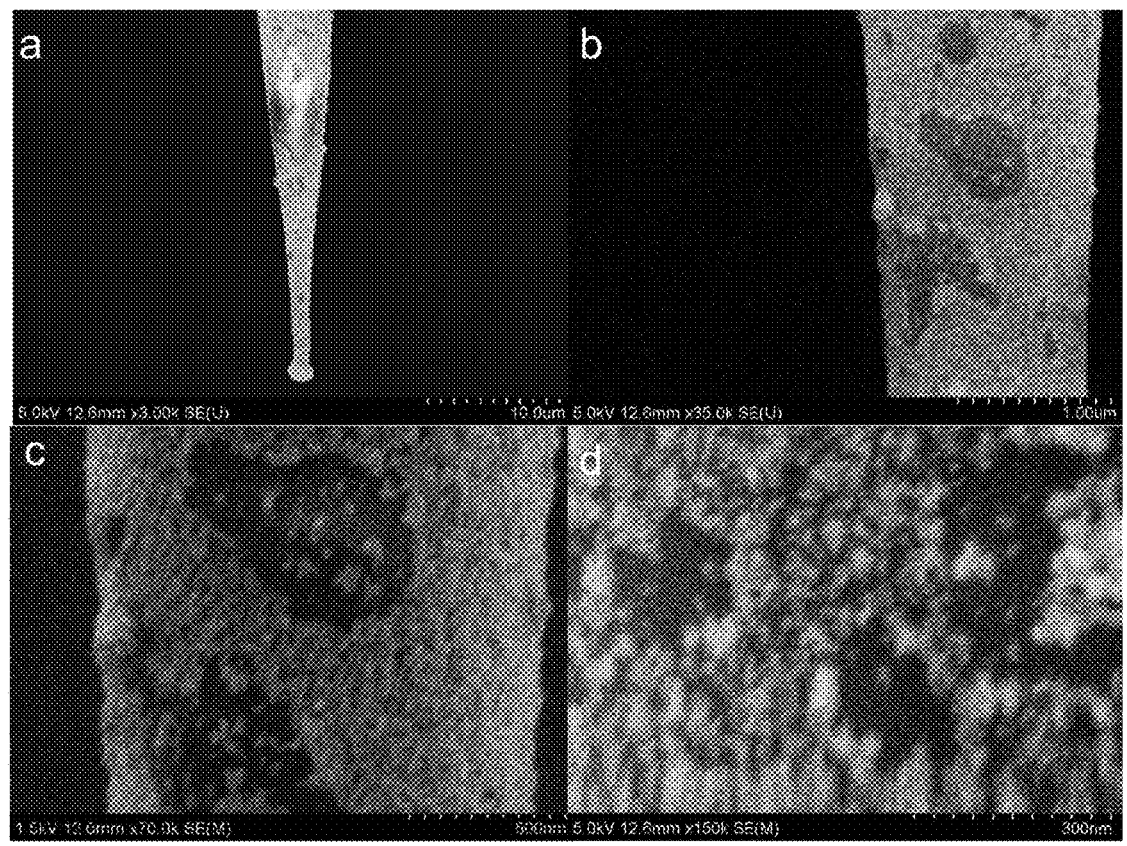
*FIG. 9A-D*

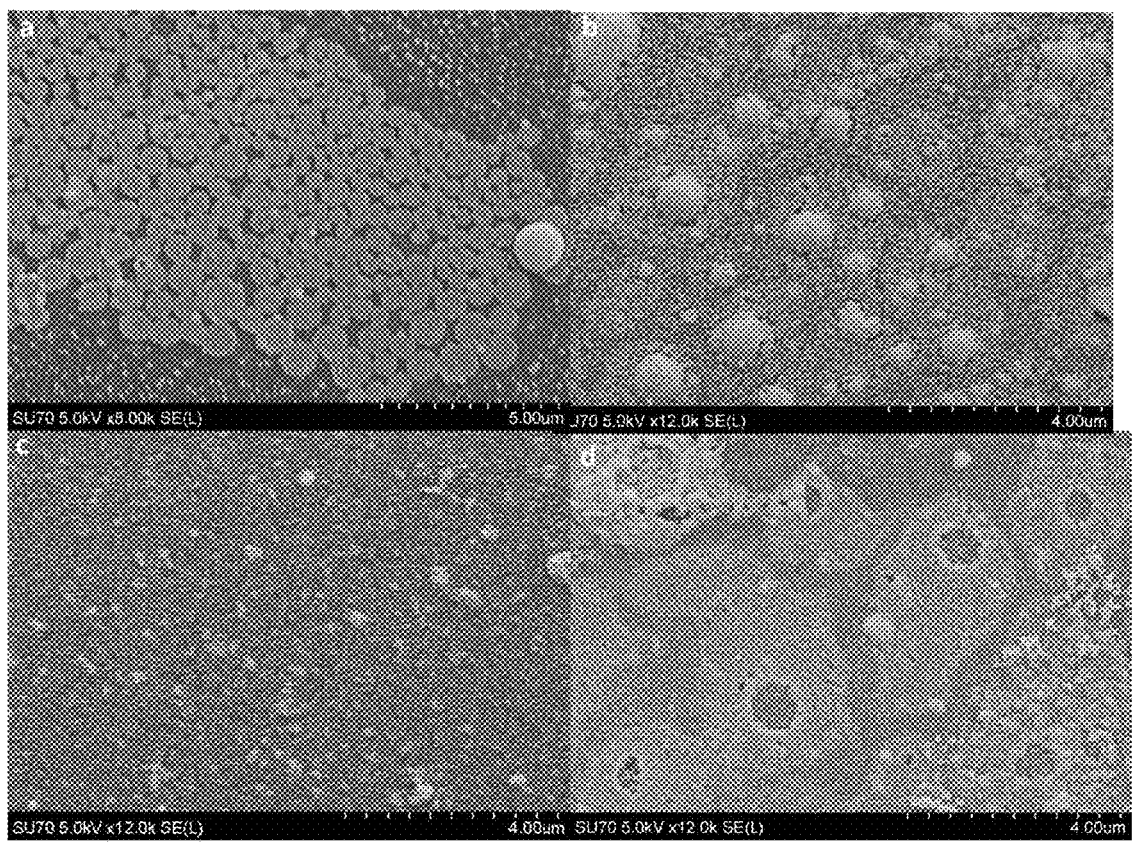
*FIG. 10A-D*

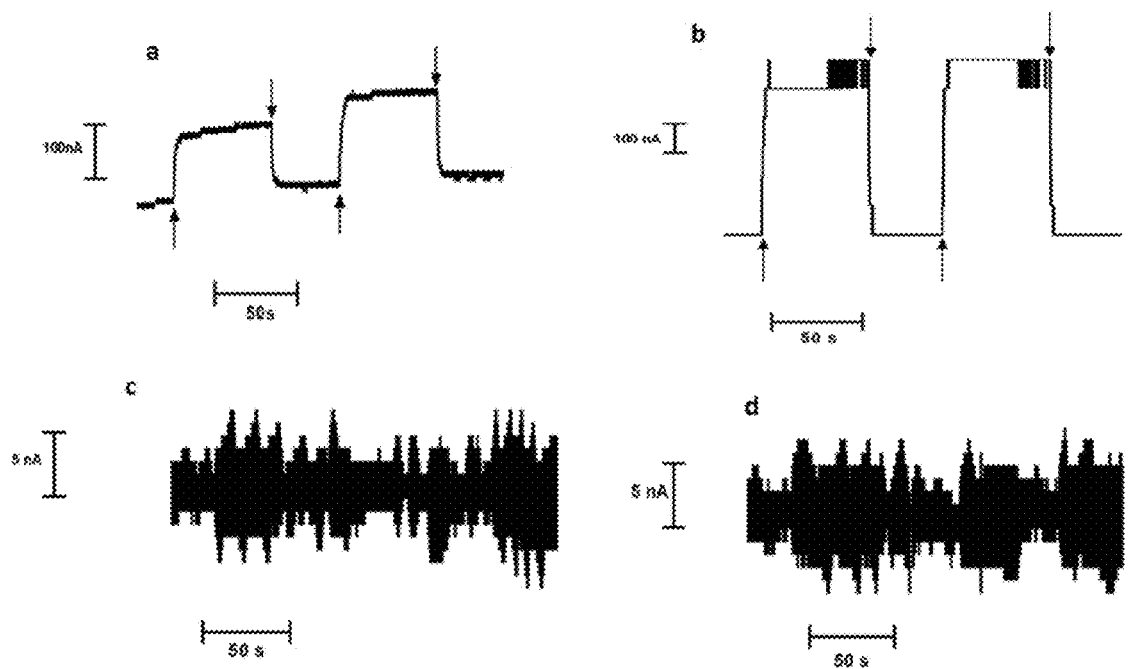
*FIG. 11A-D*
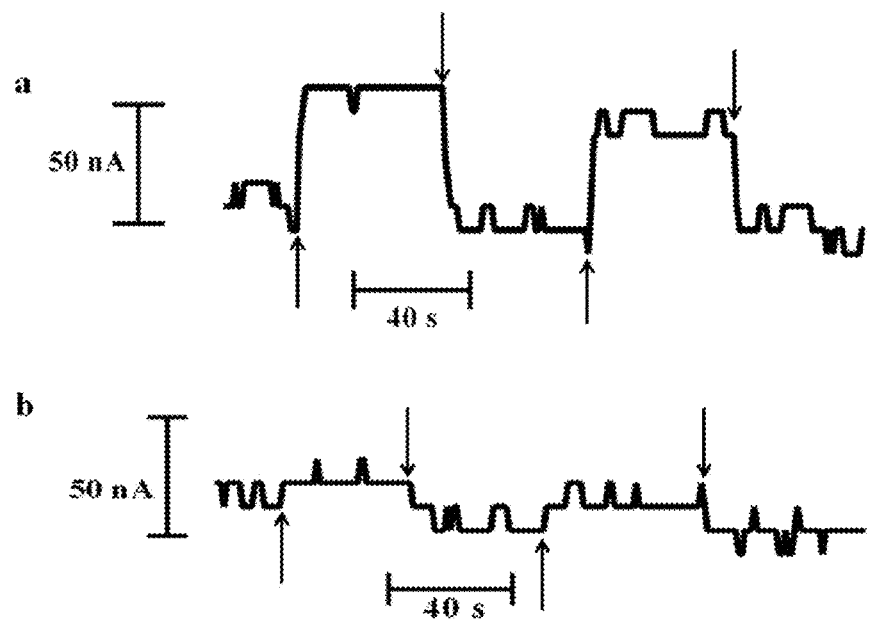
*FIG. 12A-B*

PLASMONIC STIMULATION OF ELECTRICALLY EXCITABLE BIOLOGICAL CELLS

CROSS REFERENCE TO RELATED APPLICATIONS

This application is a nonprovisional of and claims priority to U.S. Provisional Patent Application No. 62/118,103, entitled "Plasmonic Stimulation of Electrically Excitable Biological Cells", filed Feb. 19, 2015, the entire contents of which is herein incorporated into this disclosure.

GOVERNMENT SUPPORT

This invention was made with Government support under Grant No. P01 AG009524 awarded by the National Institutes of Health. The Government has certain rights in the invention.

FIELD OF INVENTION

This invention relates to stimulating cells. Specifically, the invention describes a method of stimulating electrically active biological cells using visible wavelength light.

BACKGROUND OF THE INVENTION

Most neural prosthetic devices, such as cochlear implants, retinal implants, and cardiac pacemakers, work on the principle of electrical stimulation. (Wilson, B. S., Finley, C. C., Lawson, D. T., Wolford, R. D., Eddington, D. K., and Rabinowitz, W. M. (1991). Better speech recognition with cochlear implants. Nature, 352(6332):236-238; Hornig, R., Laube, T., Walter, P., Velikay-Parel, M., Bornfeld, N., Feucht, M., Akguel, H., Rssler, G., Alteheld, N., Notarp, D. L., Wyatt, J., and Richard, G. (2005). A method and technical equipment for an acute human trial to evaluate retinal implant technology. Journal of Neural Engineering, 2(1): S129; Epstein, A. E., DiMarco, J. P., Ellenbogen, K. A., Estes, N. M., Freedman, R. A., Gettes, L. S., Gillinov, A. M., Gregoratos, G., Hammill, S. C., Hayes, D. L., et al. (2008). Acc/aha/hrs 2008 guidelines for device-based therapy of cardiac rhythm abnormalities a report of the American college of cardiology/American heart association task force on practice guidelines (writing committee to revise the acc/aha/naspe 2002 guideline update for implantation of cardiac pacemakers and antiarrhythmia devices) developed in collaboration with the American association for thoracic surgery and society of thoracic surgeons. Journal of the American College of Cardiology, 51(21):e1-e62). Typically, these devices electrically stimulate biological cells such as peripheral and cranial nerves, vestibular hair cells, cochlear nerves, and cardiac cells.

With regard to cochlear implants, a set of electrodes are placed into the cochlea. Different electrodes stimulate different auditory nerve fibers (ANFs) via current pulses based on sound frequencies with high frequencies towards the base of the cochlea and low frequencies towards the apex of the cochlea, thus mimicking the tonotopic organization of the cochlea. Because of electrical current spread, it is difficult to stimulate discrete ANFs according to respective frequencies. Specifically, the processing of speech in background noise and musical sounds to the desired perception of cochlear implant users still remains a significant problem to be addressed because, normally, speech and music has a large number of frequencies at various volume/intensity levels. (O'Leary, S. J., Richardson, R. R., and McDermott, H. J. (2009). Principles of design and biological approaches for improving the selectivity of cochlear implant electrodes. Journal of Neural Engineering, 6(5):055002; Firszt, J. B., Koch, D. B., Downing, M., and Litvak, L. (2007). Current steering creates additional pitch percepts in adult cochlear implant recipients. Otology & Neurotology, 28(5):629-636; Limb, C. J. and Roy, A. T. (2014). Technological, biological, and acoustical constraints to music perception in cochlear implant users. Hearing Research, 308(0):13-26. Music: A window into the hearing brain).

Peripheral neuropathy is a condition related to the damage and/or malfunctioning of a nerve or a group of nerves of the peripheral nervous system. Electromyography is one of the most common techniques used to detect or diagnose peripheral neuropathy. Like cochlear implants, electromyography also works on the principle of electrical stimulation of muscles/nerves. As electrical stimulation is not specific, it will not stimulate a single nerve but large groups of peripheral nerve bundles. Interestingly, there are recent reports that infrared lasers can invoke in vivo responses. Wells et al. (2005) reported 2 to 10 µm wavelength infrared lasers invoked responses from rat sciatic nerve. (Wells, J., Kao, C., Jansen, E. D., Konrad, P., and Mahadevan-Jansen, A. (2005). Application of infrared light for in vivo neural stimulation. Journal of Biomedical Optics, 10(6):064003-064003-12). The likely mechanism of infrared stimulation is a temperature rise due to photothermal interaction and membrane capacitance changes. (Wells, J., Kao, C., Konrad, P., Milner, T., Kim, J., Mahadevan-Jansen, A., and Jansen, E. D. (2007). Biophysical mechanisms of transient optical stimulation of peripheral nerve. Biophysical Journal, 93(7):2567-2580; Shapiro, M. G., Homma, K., Villarreal, S., Richter, C.-P., and Bezanilla, F. (2012). Infrared light excites cells by changing their electrical capacitance. Nature Communications, 3:736).

Infrared lasers can also be used to stimulate auditory nerve fibers (ANFs) of deaf animals, giving better spatial resolution as compared to electrical stimulation. (Izzo, A. D., Richter, C.-P., Jansen, E. D., and Walsh, J. T. (2006). Laser stimulation of the auditory nerve. Lasers in Surgery and Medicine, 38(8):745-753; Izzo, A. D., Walsh, J. T., Jansen, E. D., Bendett, M., Webb, J., Ralph, H., and Richter, C.-P. (2007b). Optical parameter variability in laser nerve stimulation: a study of pulse duration, repetition rate, and wavelength. Biomedical Engineering, IEEE Transactions on, 54(6): 1108-1114; Littlefield, P. D., Vujanovic, I., Mundi, J., Matic, A. I., and Richter, C.-P. (2010). Laser stimulation of single auditory nerve fibers. The Laryngoscope, 120(10): 2071-2082; Rajguru, S. M., Matic, A. I., Robinson, A. M., Fishman, A. J., Moreno, L. E., Bradley, A., Vujanovic, I., Breen, J., Wells, J. D., Bendett, M., et al. (2010). Optical cochlear implants: evaluation of surgical approach and laser parameters in cats. Hearing Research, 269(1): 102-111).

Shapiro et al. (2012) showed that the absorption of infrared laser energy causes a local temperature rise which does not affect a particular membrane channel directly, but rather changes cell membrane capacitance. However, along with the neurons, the infrared laser increases the temperature of the surrounding tissue as well, which can cause thermal damage or unwanted stimulation.

The inventors sought to develop an alternative technology to electrical stimulation with a special focus on stimulation of neurons, cardiomyocytes, auditory nerve fibers, and for applications to diagnosing and treating peripheral neuropathy. The inventors show herein that plasmonic heating can be used to stimulate electrically excitable biological cells with localized heating and without the bulk heating that is present when infrared light is used.

Nanoparticles are a fundamental building block of nanotechnology and find applications in various fields like electronics, chemistry, catalysis, pharmaceuticals, biology, etc. (Shipway, A. N., Katz, E., and Willner, I. (2000). Nanoparticle arrays on surfaces for electronic, optical, and sensor applications. *Chem Phys Chem*, 1(1):18-52; Daniel, M.-C. and Astruc, D. (2004). Gold nanoparticles: assembly, supramolecular chemistry, quantum-size-related properties, and applications toward biology, catalysis, and nanotechnology. *Chemical Reviews*, 104(1):293-346; Otsuka, H., Nagasaki, Y., and Kataoka, K. (2003). Pegylated nanoparticles for biological and pharmaceutical applications. *Advanced Drug Delivery Reviews*, 55(3):403-419; Salata, O. V. (2004). Applications of nanoparticles in biology and medicine. *Journal of Nanobiotechnology*, 2(1):3).

Nanoparticles are defined as particles having a diameter less than 100 nm. (Kruis, F. E., Fissan, H., and Peled, A. (1998). Synthesis of nanoparticles in the gas phase for electronic, optical and magnetic applications a review. *Journal of Aerosol Science*, 29(5):511-535). Their physical and chemical properties change dramatically with particle size. Metallic nanoparticles, such as gold (Au) nanoparticles, have strong surface interactions with electromagnetic fields because of the relative availability of free electrons in conduction bands. In surface plasmon resonance (SPR), light, which is an electromagnetic wave, interacts with metal nanoparticles causing conduction band electrons to oscillate. The oscillation becomes maximum at a particular wavelength of light. (FIG. 1) The SPR peak can be tuned with particle properties, such as size and shape. For gold nanoparticles, the SPR peak is at about 520 nm. Gold nanoparticles absorb and scatter light very efficiently. For example, for small size particles (<20 nm in diameter), absorption dominates. As size increases, scattering efficiency increases because higher-order electron oscillations start to play a significant role. As gold nanoparticles are not good emitters of light, absorbed light generates heat. (Coronado, E. A., Encina, E. R., and Stefani, F. D. (2011). Optical properties of metallic nanoparticles: manipulating light, heat and forces at the nanoscale. *Nanoscale*, 3:4042-4059; Huang, X. and El-Sayed, M. A. (2010). Gold nanoparticles: optical properties and implementations in cancer diagnosis and photothermal therapy. *Journal of Advanced Research*, 1(1): 13-28). This localized heating due to SPR is also known as plasmonic heating. Thus, for local heating applications small size Au particles (20 nm and smaller) are used, while for scattering applications like imaging, larger particles are utilized (30 nm and larger).

Given the difficulties in the current state of the art at the time of the invention, the inventors examined if localized SPR can be used to stimulate electrically excitable biological cells such as neurons or cardiomyocytes utilizing visible light as the energy source. The inventors investigated stimulation of cardiomyocytes (from neonatal rats) and SH-SY5Y mammalian neurons using gold nanoparticles and visible light.

SUMMARY OF INVENTION

Most neural prosthetic devices, such as cochlear implants, retinal implants and cardiac pacemakers, work on the principle of electrical stimulation. The electric fields produced by the electric currents spread, resulting in low spatial resolution. The electrodes are invasive and over time repeated stimulation can lead to tissue damage.

This invention presents an alternative wireless technology using plasmonic phenomena in metallic nanoparticles and visible wavelength light sources. Using the technology disclosed in this invention, non-invasive stimulation using visible wavelength light sources can be achieved for these prosthetic devices. This technology also has applications in fine brain and neural mapping, and in fine detail neural, cardiac and pain ablation research.

The inventors have developed a method to stimulate electrically active biological cells using visible wavelength light. Metallic nanoparticles possessing plasmonic properties are utilized in this invention. These particles can be tuned to respond to specific wavelength light sources. Electrically active cells, such as neurons and cardiomyocytes, can be stimulated to produce physiological voltage responses, such as action potentials. This allows for the construction of prosthetic devices, such as cochlear implants or retinal prosthetics, with superior spatial resolution relative to currently used electrical electrode-based stimulation. Implants using the novel technology possess superior properties, including better spatial and temporal resolution; at-a-distance, non-invasive stimulation; and wider design parameter space using different nanoparticles and wavelengths of light.

In an embodiment, plasmonic gold nanoparticles of about 20 nm diameter are coated on a micropipette electrode typically used for patch-clamp experiments. A green laser emitting at 532 nm wavelength is utilized to excite surface plasmons in these nanoparticles. When placed near SH-SY5Y neurons and cardiomyocytes from neonatal rats (at about 2 micrometers) in vitro, several types of plasmonic stimulation responses were observed. Plasmonic stimulation initiates action potentials in both types of cells. For the SH-SY5Y cells stimulated with 10 ms or longer laser pulses, increases in the cell membrane potential (plasmonic jumps) were observed. These increases change in magnitude relative to the holding potential for each cell. The cells were found to fire action potentials before and after the plasmonic stimulation experiment, indicating that the cell was viable and healthy. Similar plasmonic jumps were observed for neonatal cardiomyocytes. Firing of action potentials has been realized in these two types of bio-electroactive cell types. A mathematical model for predicting the electric field distribution and temperature distribution allows for optimization of the laser pulses. Such a model solves the electromagnetic equations using computer simulation using methods such as the Finite Difference Time Domain (FDTD), and heat transfer and fluid flow models utilizing energy balances coupled with the Navier-Stokes equations. The former would give the electric field distribution and the latter the temperature distribution.

Plasmonic stimulation has several advantages over electrical stimulation including being highly localized thus allowing higher spatial resolution than electrical stimulation. Unlike electrical stimulation, plasmonic stimulation also does not require a wire connection between the Au nanoparticles and energy source, i.e. laser. The visible laser also does not increase the temperature of surrounding tissue like infrared stimulation. Given these potential advantages, plasmonic stimulation can revolutionize the existing field of biomedical stimulation implants and testing of muscles/nerves of peripheral nervous system that currently employ electrical stimulation.

In one embodiment, a method of stimulating electrically active biological cells is presented comprising: providing a nanoelectrode coated with metallic nanoparticles; providing an energy source capable of emitting visible wavelength light to excite the metallic nanoparticles on the nanoelectrode; positioning the nanoelectrode adjacent to the cells; focusing the energy source on the nanoelectrode; and emitting pulses of visible wavelength light from the energy source to plasmonically stimulate the cells. The electrically active biological cells can be neurons, cardiomyocytes, or retinal cells. The metallic nanoparticles can be gold nanoparticles having a diameter of about 20 nm. The energy source can be a laser emitting visible wavelength light such as a green light laser emitting light at about a 532 nm wavelength and having a power of about 100 mW and a voltage of about 20 mV. The energy source can be focused through an optical fiber to the nanoelectrode or alternatively the energy source can be focused through the use of a nanoelectrode cuff. If an optical fiber is used, it can have an inside diameter of about 50 μm. The pulses can be between about 1 ms to about 5 ms in duration. The nanoelectrode can be positioned about 2 micrometers from the cell.

In an embodiment, a method of stimulating electrically active biological cells is presented comprising: coating a microelectrode with metallic particles to create a nanoelectrode wherein the metallic nanoparticles are gold; providing a laser capable of emitting visible wavelength light to excite the nanoparticles on the nanoelectrode; providing an optical fiber to focus the visible wavelength light from the laser on the nanoelectrode; positioning the nanoelectrode adjacent to the cells; focusing the visible wavelength light from the laser on the nanoelectrode; and emitting pulses of visible wavelength light from the laser to plasmonically stimulate the cells. The nanoparticles can be about 20 nm in diameter. The laser can be a green light laser emitting pulses between 1 ms and 5 ms in duration.

Also presented is a cochlear implant comprising an external and an internal portion. The external portion is comprised of a microphone wherein the microphone obtains sound from a patient's environment; a speech processor connected to the microphone wherein the speech processor selects and arranges the sound obtained from the microphone; and a transmitter connected to the speech processor wherein the transmitter receives signals from the speech processor and sends the signals to a receiver. The internal portion is comprised of a receiver wherein the receiver receives the signals from the transmitter; a laser, such as a green light laser, capable of emitting visible wavelength light connected to the receiver wherein the laser codes the signals from the receiver into light pulses; an optical fiber connected to the laser wherein the optical fiber focuses the visible wavelength light from the laser onto at least one nanoelectrode; at least one nanoelectrode connected to the optical fiber wherein the nanoelectrode is activated by the light pulses produced by the laser; wherein the activated nanoelectrode plasmonically stimulates auditory nerve cells to enable the patient to hear the sounds.

BRIEF DESCRIPTION OF THE DRAWINGS

For a fuller understanding of the invention, reference should be made to the following detailed description, taken in connection with the accompanying drawings, in which:

FIG. 1 is an image depicting SPR.

FIG. 5A-B are images illustrating digital micrographs showing the plasmonic set up in which the nanoelectrode was placed just next to a SH-SY5Y cell and another microelectrode was used to patch the cell in whole cell configuration. An optical fiber having inside diameter 50 μm was used to focus the laser on the tip of the nanoelectrode (a) when laser was off and (b) when laser was on.

FIG. 7A-B is an image depicting SEM images of gold nanoparticles: (a) a 100 nm scale bar and (b) a 50 nm scale bar.

FIG. 8 is a TEM image of gold nanoparticles (scale bar of 200 nm).

FIG. 9A-D are SEM images of the nanoelectrode, a micropipette coated with gold nanoparticles: (a) 10 μm scale bar, (b) 1 μm scale bar, (c) 500 nm scale bar, and (d) 300 nm scale bar.

FIG. 10A-D is a series of micrographs depicting SEM images of four different nanoelectrodes. It appears that gold nanoparticles were coated on the surface of the microelectrode as multilayers. SEM images of four different nanoelectrodes are presented, showing the multilayers of gold nanoparticles on the microelectrode surface (a) 5 μm scale bar; (b-d) 4 μm scale bars.

FIG. 11A-D is a series of images depicting photocurrents vs. time in 0.1 M Phosphate buffer having 0.05 M EDTA for (a) a microelectrode coated with gold nanoparticles when 0.3 V vs $Ag_{(s)}$/AgCl, reference electrode was applied (b) a microelectrode coated with gold nanoparticles when 0.9 V vs $Ag_{(s)}$/AgCl, reference electrode was applied (c) a microelectrode with no gold nanoparticles coating when 0.3 V vs $Ag_{(s)}$/AgCl, reference electrode was applied (d) a microelectrode with no gold nanoparticles coating when 0.9 V vs $Ag_{(s)}$/AgCl, reference electrode was applied.

FIG. 12A-B is a series of images depicting photocurrents vs. time curves in extracellular solution (a) a microelectrode coated with gold nanoparticles when 0.3 V vs $Ag_{(s)}$/AgCl, reference electrode was applied (b) a microelectrode with no gold nanoparticles coating when 0.3 V vs $Ag_{(s)}$/AgCl, reference electrode was applied.

DETAILED DESCRIPTION OF THE PREFERRED EMBODIMENT

Figure 2:
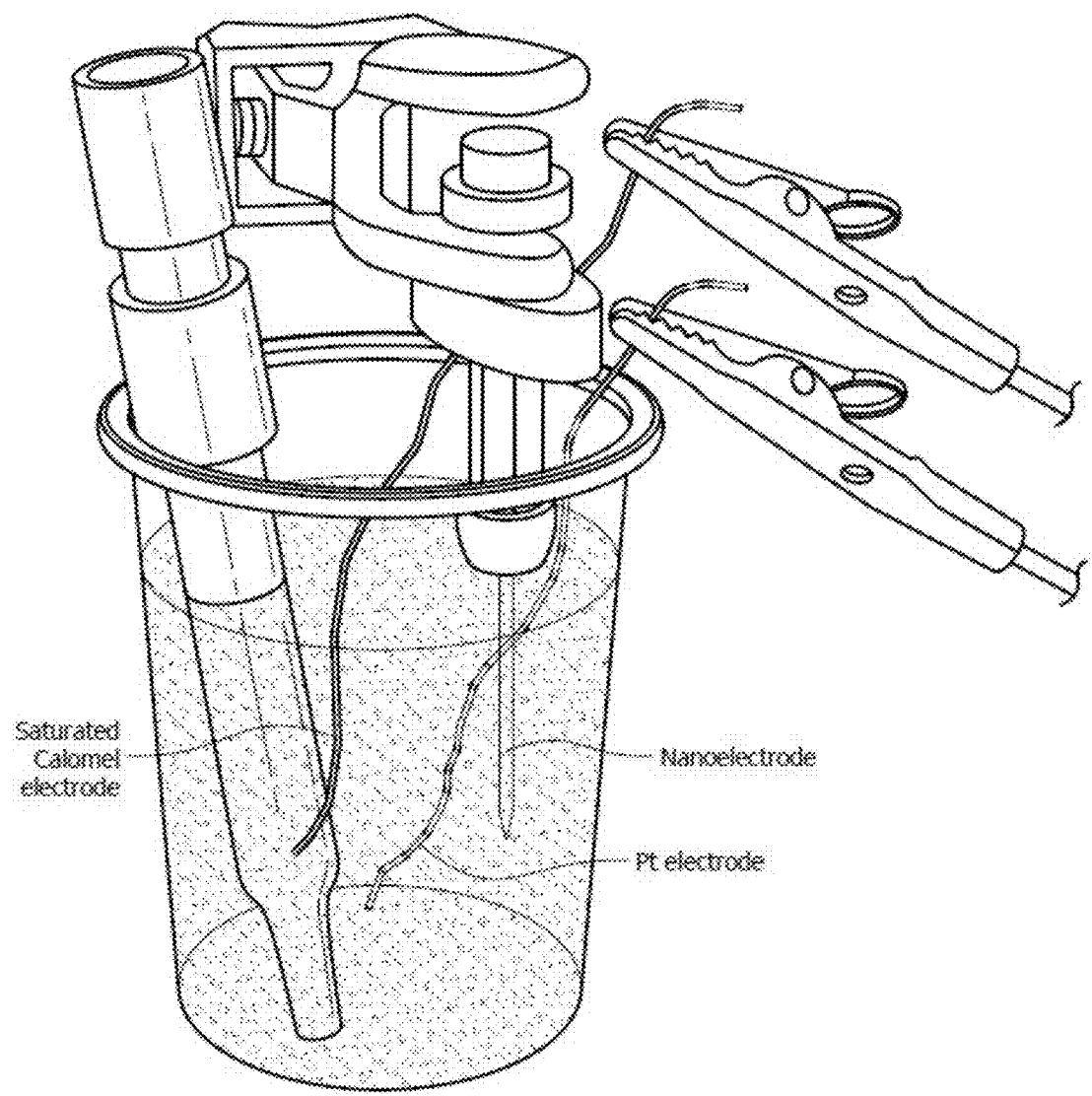
FIG. 2 is an image of a micrograph illustrating an electrochemical cell to record the photocurrent: A beaker filled with 0.1 M Phosphate Buffer/0.05 M EDTA electrolyte solution; containing the electrodes, nanoelectrode and Pt electrode, along with reference electrode: saturated calomel electrode (SCE).

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise. For example, the term "a nanoparticle" includes a plurality of nanoparticles, including mixtures thereof.

"Patient" is used to describe an animal, preferably a human, to whom treatment is administered using the method of the present invention.

"Nanoparticle" as used herein refers to a microscopic particle having at least one dimension that is less than 100 nm. Nanoparticles used herein can be metallic and have a diameter of about 20 nm or less. Metallic nanoparticles used herein include, but are not limited to, silver, gold, copper, aluminum, palladium, and alloys thereof including bimetallic nanoparticles. Alloy composition, size of the nanoparticle, shape of the nanoparticle (cubic, spherical, rod-like, etc) are some parameters which allow for tuning the wavelength at which plasmonic phenomena occurs in these nanoparticles. In an embodiment, the nanoparticles have a diameter of about 20 nm and are gold nanoparticles. "Plasmonic nanoparticle" as used herein refers to a metal nanoparticle that is highly efficient at absorbing and releasing the light as scattered light or as heat, depending upon the nanoparticle properties (shape, size, composition, etc.).

"Tuning" as used herein refers to changing the size, shape, surface chemistry or aggregation state of a nanoparticle in order to optimize the optical and electronic properties of the nanoparticle to a particular application. The plasmonic peak can be tuned to any wavelength by a suitable design of the nanoparticles as discussed in U.S. Pat. No. 9,005,890, herein incorporated in its entirety by reference.

"Surface plasmon" or "surface plasmon resonance" as used herein refers to resonant oscillations of oscillating electric fields of a ray of light propagating near a colloidal nanoparticle that interact with the free electrons thus causing an oscillation of electron charge that is in resonance with the frequency of visible light.

"Nanoelectrode" as used herein refers to a microelectrode coated with metallic nanoparticles. In some embodiments, the metallic nanoparticles are gold and the microelectrode is a glass pipette.

"Energy source" as used herein refers to an object capable of emitting visible wavelength light, such as a laser or light emitting diode. In some embodiments, the energy source is a laser which emits light at a wavelength near the SPR peak of the metallic nanoparticle. For example, a green light laser may be used as the energy source when the metallic nanoparticle is made of gold since the green light laser emits visible light at a wavelength near the SPR peak of a gold nanoparticle.

"Visible wavelength light" refers to light having wavelengths between about 400 nm to about 800 nm. The wavelength of the utilized light is dependent upon the surface plasmon resonance (SPR) peak of the nanoparticle. The composition of the nanoparticle, as well as its size and shape, will, in part, define the SPR peak of the nanoparticle. The visible wavelength light used is dependent on the SPR of the nanoparticle. For example, in some embodiments where spherical 20 nm diameter gold nanoparticles are used, the wavelength is about 532 nm. While the invention is discussed herein as using the visible light range, plasmonic phenomena can be evoked in the ultraviolet and in the infrared range as well (below 400 nm and above 800 nm). For example, gold nanorods can be tuned to have plasmonic peaks in the infrared range (900 to 1200 nm, for example) and such light can be used in the invention herein as well. However, it should be noted that ultra violet (UV) light may damage the cells, hence very low intensity may be necessary.

Figure 23:
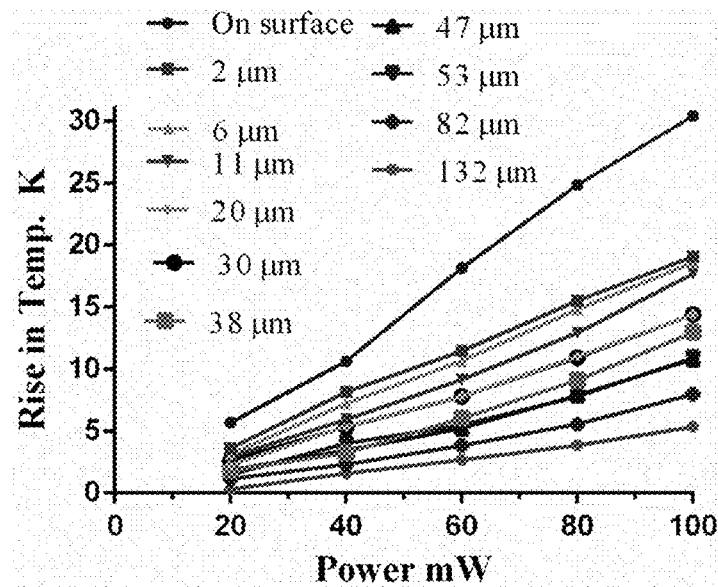
FIG. 23 is an image depicting the rise in temperature vs laser power at different distances away from the nanoelectrode.

"Adjacent" as used herein when referring to the positioning of the nanoelectrode to the cell, is defined as the distance between the nanoelectrode and the cell being on the order of varying only by a few microns. This distance is dependent on the power of the visible light used. As the power of the light increases, as does the distance between the nanoelectrode and the cell. (FIG. 23) A local rise in temperature decreases with an increase in distance away from the nanoelectrode. For example, the term "adjacent" is meant to cover distances of 0 (meaning the nanoelectrode is touching the cell) up to a distance of 6 μm from the cell. It is preferable that the nanoelectrode is as close as possible to the cell without disturbing the cell. In some embodiments in which a green light laser emitting light at 532 nm is used, the nanoelectrode is placed 2 μm from the cell.

"Pulse" as used herein refers to the amount of time the energy source is emitting light. In order to fire action potentials, a pulse width (individual pulse duration) of between about 1-5 ms was used. The pulse width can be correlated to the shape/size of the nanoparticles as well as the laser wavelength/power. A single pulse of between 1-5 ms was used in some of the examples described herein, however two pulses may also be administered with a gap of about 50-100 ms between the pulses. With a pulse width of 10 ms or more, jumps in membrane potential were observed. These results indicate that cells fire action potentials for laser pulses that are less than 10 ms in duration. As timing increases to 10 ms and above, there is less of a chance in achieving an action potential thus the pulse width for the size/shape of the nanoparticles used in the examples described herein should be less than 10 ms. For devices such as cochlear implants, a pulse width of between about 1-5 ms is used.

To achieve inhibition, laser pulses were superimposed on the electrical pulse with a timing of 300 ms. Current electrical stimulation is used not only for activation but for cases where cells have high activities like in case of brain trauma. The inhibition experiment was done to demonstrate that when laser pulse is super imposed on electrical pulse, then, there is suppression in action potential magnitude. Pulse timing is equal to the timing of electrical pulse, thus it can be more than 300 ms as well. Also, suppression of the action potential is more prominent when the laser is pre-pulsed to electrical pulse by few milliseconds (5-10 ms).

Materials and Methods

Synthesis of Gold Nanoparticles

Gold (Au) nanoparticles were synthesized by a standard citrate method that involves reduction of a gold salt solution (Chloroauric acid) using a sodium citrate solution (Nath, N. and Chilkoti, A. (2002). A colorimetric gold nanoparticle sensor to interrogate biomolecular interactions in real time on a surface. *Analytical Chemistry,* 74(3):504-509). Specifically, the glass beakers were washed thoroughly first with distilled water, then, with ethanol. 20 ml of 0.01 mM chloroauric acid ($HAuCl_4$) was boiled on a heating plate with continuous stirring, using a magnetic stirrer. Next, 3 ml of 1% sodium citrate solution was added to the boiling solution ofchloroauric acid. After 10 min, the solution became a deep red in color which indicates the presence of Au nanoparticles.

Fabrication of Nanoelectrodes for Stimulation

Nanoelectrodes were fabricated by coating Au nanoparticles onto glass micropipettes. Nath and Chilkoti (2002) studied the interaction of a biomolecule with a monolayer of Au nanoparticles coated glass cover-slips. This coating involved three steps: cleaning the glass cover-slip surface, functionalization of the glass surface with γ-(aminopropyl) triethoxysilane, and finally, coating of the functionalized glass surface with gold nanoparticles. The same three steps were used to coat gold nanoparticles onto glass micropipettes, as explained below.

Cleaning of Micropipettes

The glass micropipettes were put inside a petri-dish and washed using liquid detergent with continuous heating at 55-60° C. for 10-15 min. The micropipettes were thoroughly washed with distilled (DI) water to remove detergent. The micropipette was cleaned with 1:1 v/v (volume/volume)

solution of HCl and methanol for 30 min, and subsequently, washed with DI water thoroughly. Micropipettes were dried overnight at 60° C. in an oven.

Functionalization of the Micropipettes with γ-(Aminopropyl) Triethoxysilane

The tip of the micropipette was immersed in 10% v/v solution of γ-(aminopropyl) triethoxysilane in anhydrous ethanol for 15 min. Subsequently, the micropipette was washed 5 five times with ethanol and dried at 120° C. for 3 h.

Coating of Gold Nanoparticles

The functionalized micropipette tip was immersed in the gold nanoparticles solution for 24 h. The gold nanoparticle-coated micropipette was characterized using scanning electron microscopy.

Testing of Nanoelectrode

Prior to biological cell experiments, nanoelectrode responses to 532 nm green lasers were tested in electrochemical cells. Lowe et al. (2003) demonstrated that a laser-induced temperature jump occurs when a gold nanoparticle-coated indium tin oxide electrode was illuminated with a 532 nm green laser in a electrochemical cell, where, 0.1 M phosphate buffer containing 0.05 M EDTA was used as the electrolyte solution. (Lowe, L. B., Brewer, S. H., Krmer, S., Fuierer, R. R., Qian, G., Agbasi-Porter, C. O., Moses, S., Franzen, S., and Feldheim, D. L. (2003). Laser-induced temperature jump electrochemistry on gold nanoparticle-coated electrodes. *Journal of the American Chemical Society*, 125(47): 14258-14259). The maximum photocurrent was reported near the oxidation peak potential of EDTA on gold nanoparticles, 0.9 V vs $Ag_{(s)}$/AgCl. The nanoelectrode, i.e. the microelectrode coated with the gold nanoparticles, and a Pt electrode, were used as the two electrodes of the electrochemical cell whereas a saturated calomel electrode served as the reference electrode. FIG. 2 shows an electrochemical cell with two electrodes, along with the reference electrode. The control experiment was done with the microelectrode not coated with the gold nanoparticles. The same experiment was done again with extracellular solution as the electrolyte instead of phosphate buffer. When laser was shined on the tip of the nanoelectrode, a jump in circuit current was observed. There was no corresponding additional jump when experiments were done with an uncoated micropipette. Similar photocurrent jumps were observed when extracellular solution was used as the electrolyte instead of the phosphate buffer. The photocurrents increase with applied circuit voltage.

Plasmonic Temperature Measurement

Yao et al. (2009) reported a pipette resistance method, an indirect method to measure the local rapid temperature jumps that occurred during the infrared stimulation of biological cells. (Yao, J., Liu, B., and Qin, F. (2009). Rapid temperature jump by infrared diode laser irradiation for patch-clamp studies. *Biophysical Journal*, 96(9):3611-3619). In this method, a patch pipette filled with extracellular solution was placed in the petri dish containing the same extracellular solution and infrared laser was focused on the tip of the pipette with the help of an optical fiber. The pipette tip was placed near to the fiber, approximately at a distance equal to the distance between the fiber and cell for stimulation experiments. The resistance of the pipette was measured in response to a current pulse. A sudden change in resistance was obtained when the infrared laser pulse was applied on to the tip of the pipette. A pipette resistance vs temperature calibration curve was obtained by putting the pipette filled with extracellular solution into a petri dish containing hot extracellular solution and allowing it to cool down. The resistances measured during the infrared laser experiment were converted into temperature changes using the calibration curve (Shapiro et al., 2012).

Figure 3:
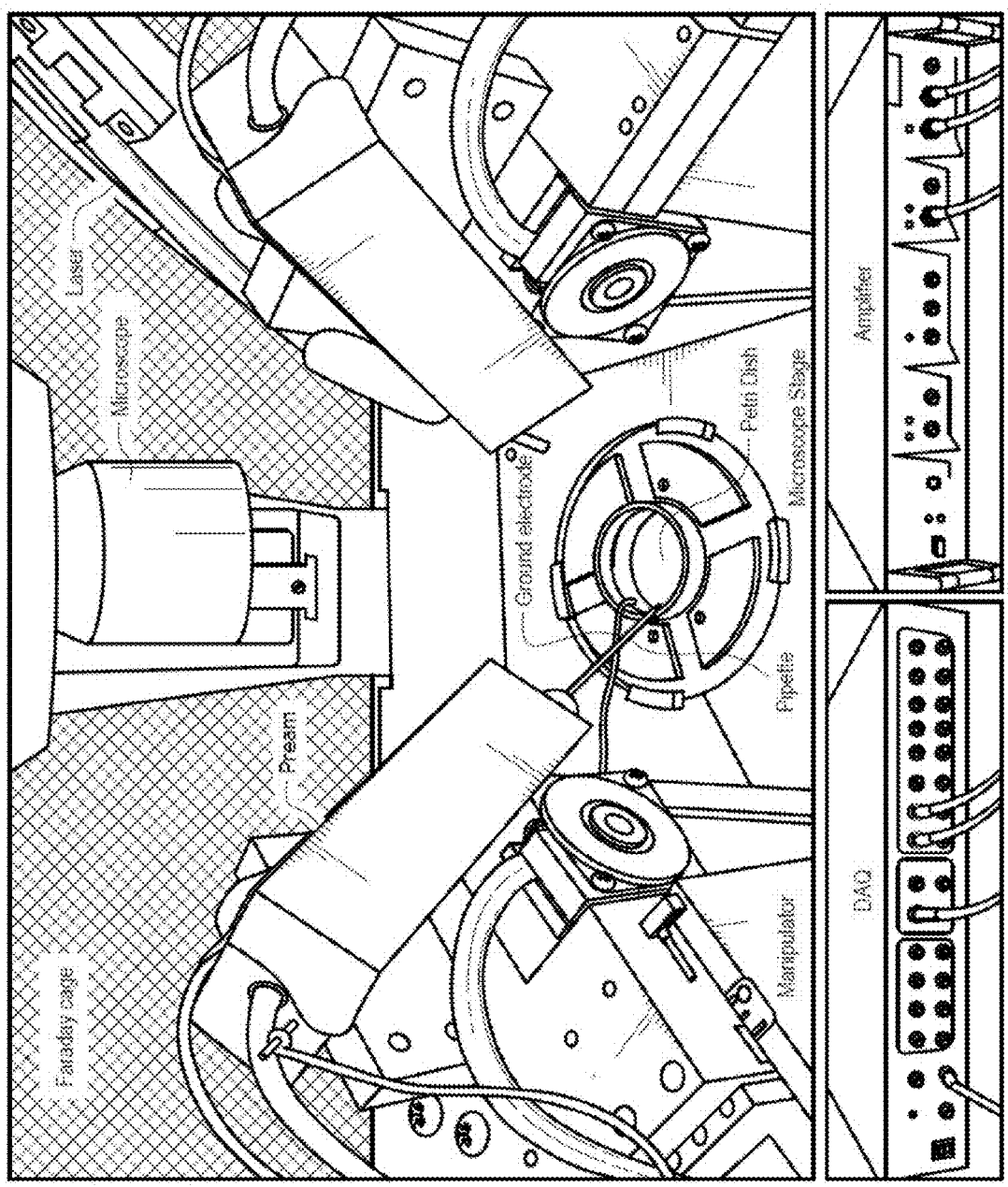
FIG. 3 is an image illustrating the patch clamp setup.
Figure 4:
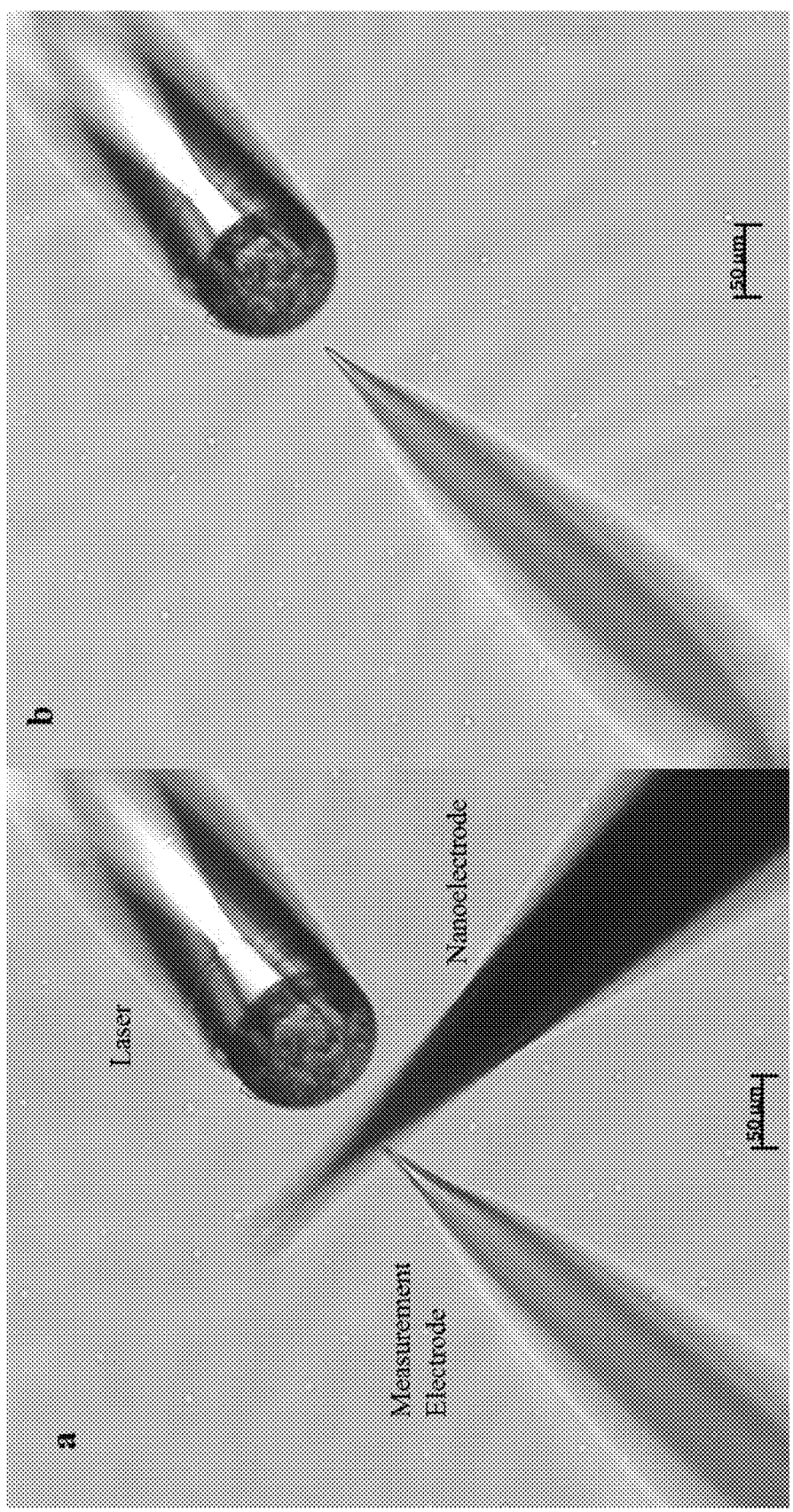
FIG. 4A-B are images depicting digital micrographs taken during the plasmonic temperature measurement at the surface of nanoelectrode. (a) The plasmonic temperature measurement experiment showing the nanoelectrode, a patch pipette filled with extracellular solution, known as the measurement electrode, placed near the nanoelectrode surface; and a 50 μm inside diameter optical fiber used to focus a 532 nm green laser on the surface of the nanoelectrode (b) The control experiment showing the measurement electrode and a 50 μm inside diameter optical fiber.

In the present investigation, the same method was used to measure the plasmonic temperature change on the surface of nanoelectrode when a 532 nm green laser was focused on the tip of the nanoelectrode using an optical fiber having a 50 μm inside diameter. The experiment was done using the patch clamp system as shown in FIG. 3 (Multiclamp 700B amplifier and Digidata 1440A data acquisition system from Molecular Devices). The resistance versus temperature calibration curve was obtained by allowing the extracellular solution to cool down from approximately 55° C. to room temperature. As the extracellular solution cools down, corresponding patch pipette resistances were measured in response to a 20 mV voltage pulse. Then, a patch pipette having 5-8 MΩ resistance, filled with extracellular solution was placed very near to the surface of the nanoelectrode, and changes in resistance were measured when a 532 nm green laser was focused on the tip of the nanoelectrode. The control experiment was done without the nanoelectrode, and no resistance change was observed in response to a 20 mV pulse. FIG. 4 shows the set-up for two experiments: a) the plasmonic temperature measurement and b) the control experiment.

Cell Culture

Neonatal Cardiomyocytes Culture 2-3 days old Sprague Dawley rat pups (8-10) were decapitated and their hearts were removed. The hearts were transferred to ice cold PBS with 20 mM glucose. The atria were removed using small scissor to get the ventricular cardiomyocytes. The ventricles were minced into small pieces and transferred into a 50 ml Falcon tube. 7 ml of type-II collagenous solution was added to the tube. After that, the tube was heated in a water bath maintained at 37° C. for 5-6 minutes with gentle shaking. The supernatant was transferred to another 50 ml Falcon tube. Next, 7 ml of the stop solution was added to the tube containing supernatant. The stop solution was M199 media with 5% FBS and 0.1% PenStrep. 7 ml of type-II collagenous solution was added into the first tube having the remaining undigested ventricular cardiomyocytes. The tube with the collagenous solution was again heated in a 37° C. water bath for 5-6 min with gentle shaking. Then, the supernatant was transferred to the tube containing the earlier digested supernatant and stop solution mixture. 7 ml of stop solution was added to make the collagenous solution inactive. The procedure was repeated until cells were digested completely. The tubes containing digested cardiomyocytes were centrifuged at 3000 rpm for 2-3 minutes. The cell pellets were re-suspended into PBS and centrifuged again at 2500 rpm for 2-3 minutes. The pellets were suspended into 13 ml day 1 medium. The day 1 medium was M199 containing 5% FBS, 10% horse serum and 0.1% PenStrep. The solution was incubated at 37° C. with 5% $CO_2$ for 1 h.

Next, the supernatant was diluted with day 1 medium and incubated in 35 mm laminin-coated petri-dishes at 37° C. with 5% $CO_2$ for 24 h. On day 2, dishes were washed with PBS twice and the day 2 medium was used. The day 2 medium had the same composition as the day 1 medium except for the amount of FBS. It contained 1% FBS instead of 5% FBS. The medium was changed every 24-48 h. The cardiomyocytes showed spontaneous beating on day 3. It has been previously shown that these cells can be used for patch clamp experiments at day 2 to day 5. (Salameh, A. and Dhein, S. (2005). Culture of neonatal cardiomyocytes. In Dhein, S., Mohr, F., and Delmar, M., editors, *Practical Methods in Cardiovascular Research*, pages 568-576).

Differentiation of SH-SY5Y Neuroblastoma Cells

SH-SY5Y (ATCC® CRL-2266) neuroblastoma cell lines can be differentiated to neurons in the presence of retinoic acid. The cells were initially cultured in a medium which is a mixture of F12 & DMEM (1:1, v/v) containing 10% FBS and 1% PenStrep at 37° C. with 5% $CO_2$. The medium was changed every 4-7 days. After 80-90% confluence, the trypsin was added to detach the cells. The cells in trypsin solution were incubated for 1-2 minute. Then, an equal volume of medium, DMEM:F12 (1:1 v/v) with 10% FBS & 1% PenStrep, was added to neutralize the trypsin. The cells were centrifuged at 1500 rpm for 5 min. Next, the cell pellet was suspended in 90% FBS, 10% DMSO for long-term storage in 1.5 ml screw cap vials in a liquid nitrogen cylinder. For the subculture, cell pellets were suspended in medium, DMEM:F12 (1:1, v/v), 10% FBS, 1% PenStrep. After 48 h of plating, the medium was replaced with the Neurobasal medium containing supplements B27 and GlutaMAX. 10 µM all-trans-retinoic acid (ATRA) was added to this medium to promote differentiation. Along with promoting differentiation, the retinoic acid inhibits cell growth as well. The medium was changed every 48 h. (Phlman, S., Ruusala, A.-I., Abrahamsson, L., Mattsson, M. E., and Esscher, T. (1984). Retinoic acid-induced differentiation of cultured human neuroblastoma cells: a comparison with phorbolester-induced differentiation. *Cell Differentiation*, 14(2): 135-144; Kovalevich, J. and Langford, D. (2013). Considerations for the use of sh-sy5y neuroblastoma cells in neurobiology. In Amini, S. and White, M. K., editors, *Neuronal Cell Culture*, volume 1078 of *Methods in Molecular Biology*, pages 9-21).

Electrophysiology

Figure 5:
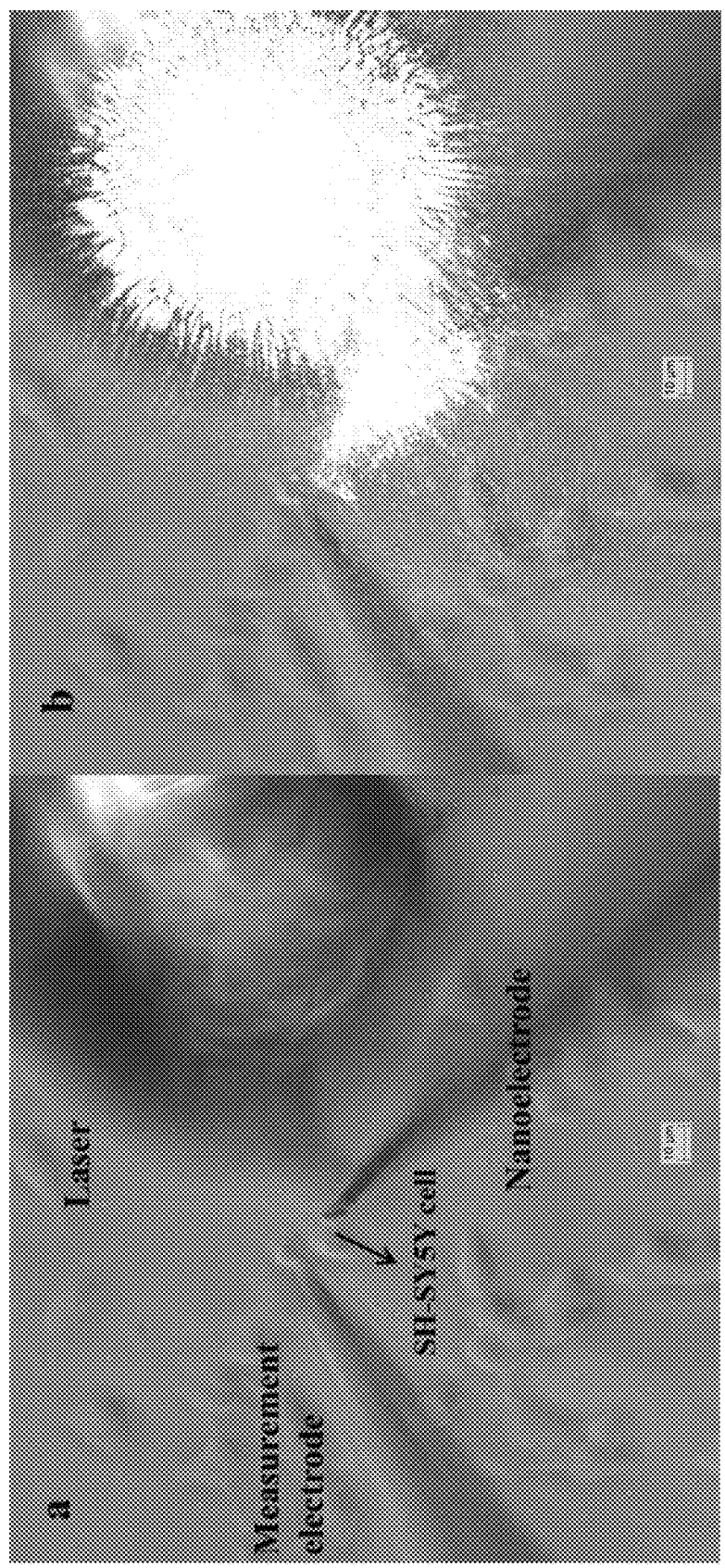

All the physiological experiments were done using the whole cell configuration of the patch clamp technique, as shown in FIG. 3 (Multiclamp 700B amplifier and Digidata 1440A data acquisition system from Molecular Devices). For plasmonic stimulation, the nanoelectrode was placed adjacent (2 µm) to the cell, while the cell was patched in whole cell configuration using another microelectrode to measure the plasmonic responses. 532 nm green laser pulses were focused on the nanoelectrode using an optical fiber with a 50 µm inside diameter. FIG. 5 shows the micrographs of one such plasmonic stimulation experiment with an SH-SY5Y cell. FIG. 5 shows the experimental set-up, where a cell was patched using the measurement electrode, nanoelectrode was placed just next to the cell and laser was focused on the tip of the nanoelectrode.

Neonatal Cardiomyocytes

Kang et al. (1995) studied the effects of fatty acids on various parameters of action potential generation of neonatal cardiomyocytes, like strength of depolarization current, cycle time and soon. (Kang, J. X., Xiao, Y. F., and Leaf, A. (1995). Free, long-chain, polyunsaturated fatty acids reduce membrane electrical excitability in neonatal rat cardiac myocytes. *Proceedings of the National Academy of Sciences*, 92(9):3997-4001).

The inventors used the control current clamp experiment protocol described in Kang et al. 1995, incorporated herein in its entirety by reference, to record action potentials from neonatal cardiomyocytes. The control experiments and plasmonic stimulation experiments were done at room temperature with no perfusion. The microelectrode resistance was 2.5-4.0 MΩ. The extracellular solution was 140 mM NaCl, 5.0 mM KCl, 1 mM $MgCl_2$, 2.0 mM $CaCl_2$, 10 mM HEPES at pH 7.4 maintained with NaOH. The intracellular solution used to fill the microelectrodes was 140 mM KCl, 2.0 mM $MgCl_2$, 1.0 mM $CaCl_2$, 5.0 mM MgATP, 10 mM NaCl, 10 mM HEPES, 10 mM EGTA, and pH 7.2 maintained with KOH.

SH-SY5Y Cells

Johansson (1994) recorded action potentials from differentiated SH-SY5Y human neuroblastoma cell lines. (Johansson, S. (1994). Graded action potentials generated by differentiated human neuroblastoma cells. *Acta Physiologica Scandinavica*, 151(3):331-341). Tosetti et al. (1998) studied the effect differentiation on potassium currents and its parameters by comparing differentiated and undifferentiated cell lines using whole-cell voltage clamp experiments. (Tosetti, P., Taglietti, V., and Toselli, M. (1998). Functional changes in potassium conductances of the human neuroblastoma cell line sh-sy5y during in vitro differentiation. *Journal of Neurophysiology*, 79(2):648-658).

Figure 24:
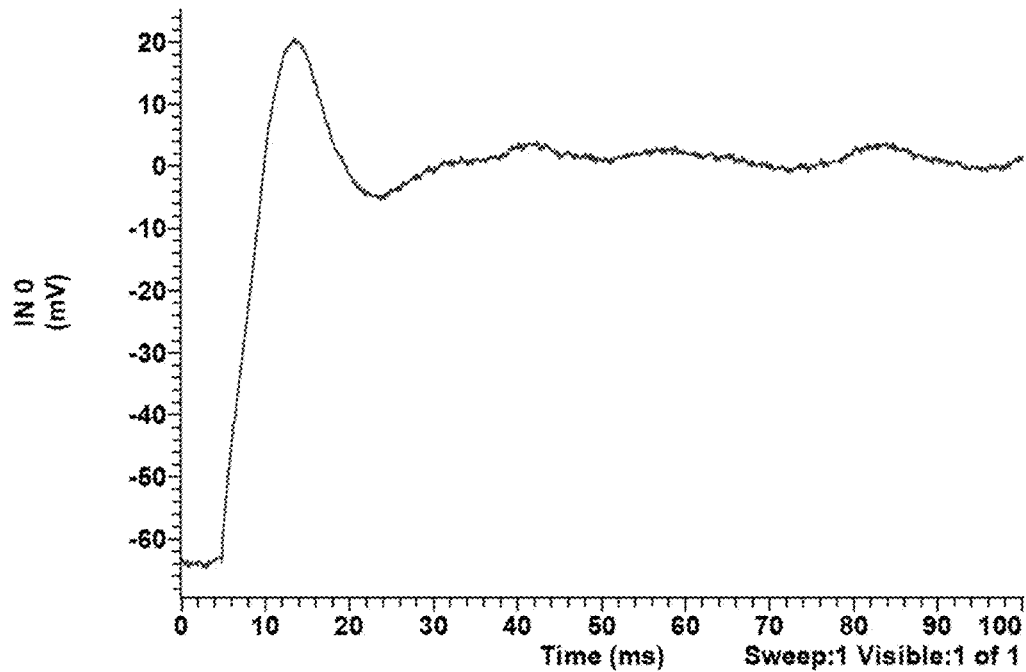
FIG. 24 is a graph depicting the action potential recorded from a SH-SY5Y cell.

The inventors recorded action potentials from undifferentiated and differentiated cell lines using the protocol of Tosetti, incorporated herein in its entirety, and also, recorded the plasmonic stimulation responses in whole cell configuration. (FIG. 24) The patch pipette had a resistance 4.5-7.5 MΩ. All the experiments were done at room temperature without perfusion.

The extracellular solution contained 125 mM NaCl, 4 mM KCl, 2 mM $CaCl_2$, 1.2 mM $MgSO_4$, 10 mM glucose, 10 mM HEPES. The pH of the extracellular solution was maintained at 7.4 using NaOH. The intracellular microelectrode solution contained 140 mM KCl, 4 mM NaCl, 0.02 mM $CaCl_2$, 0.8 mM EGTA, 2 mM $MgCl_2$, 4 mM Mg-ATP, 10 mM HEPES. The pH of the intracellular solution was maintained at 7.2 using KOH.

Characterization of Gold Nanoparticles

UV-Vis Spectra

Figure 6:
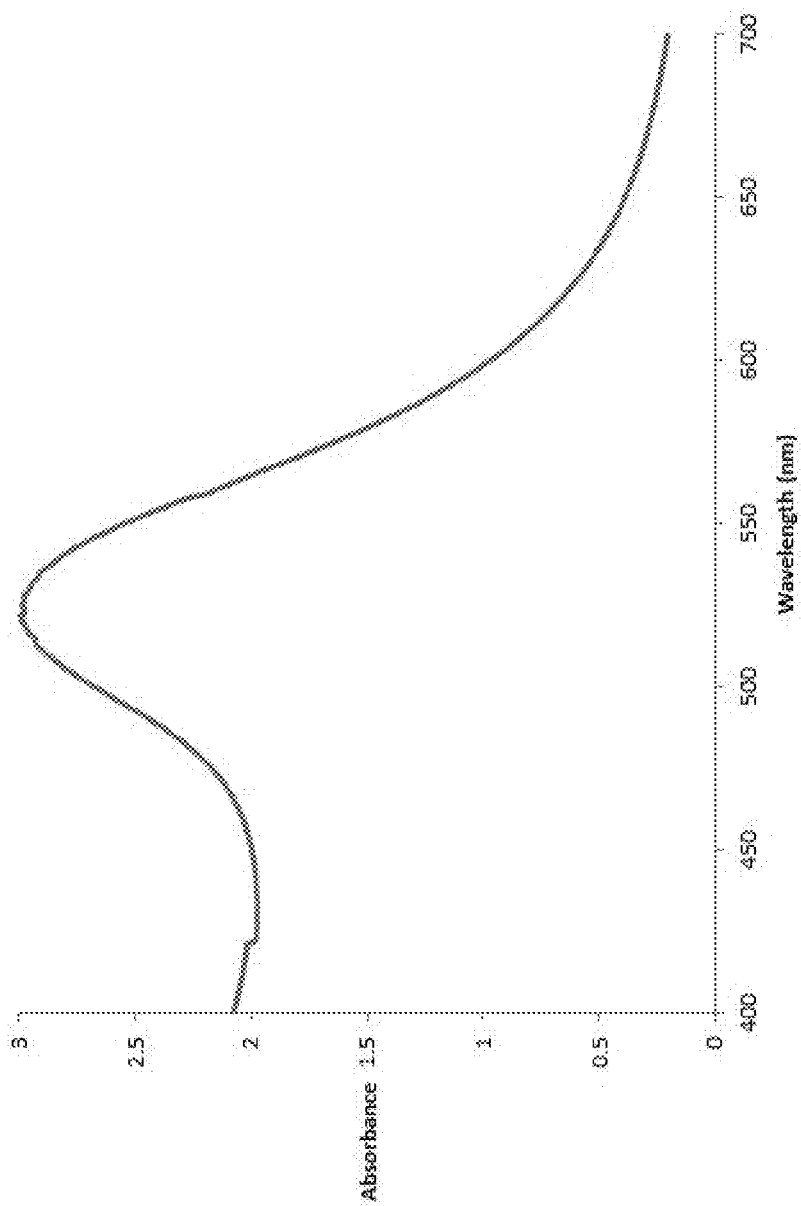
FIG. 6 is an image depicting the absorbance spectrum of gold nanoparticles.

A Perkin Elmer Lambda 35 UV/Vis spectrophotometer was used to obtain the UV/Vis spectra of the Au nanoparticles solution. FIG. 6 shows the graph relating absorbance and wavelength for the gold nanoparticles solution. The absorbance peak around 530 nm confirms the presence of Au nanoparticles.

SEM Characterization

A Hitachi S-800 scanning electron microscope (SEM) was used to image the gold nanoparticles. FIG. 7 shows the two SEM images of gold nanoparticles: at a 100 nm scale bar and at a 50 nm scale bar TEM Characterization In addition to SEM, an FEI Morgagni transmission electron microscope (TEM) was used to obtain images of gold nanoparticles. FIG. 8 represents the TEM image of gold nanoparticles at a scale bar of 200 nm.

SEA Imaging of Nanoelectrode

SEM images of gold nanoparticles coated onto a micropipette were obtained using a Hitachi SU70 SEM. FIG. 9 represents the SEM images of Au nanoparticles coated onto a micropipette (10 µm, 1 µm, 500 nm and 300 nm scale bars). SEM images clearly show the layers of gold nanoparticles coated on micropipette. FIG. 10 shows the SEM images of four different nanoelectrodes. Presence of gold nanoparticles confirms the repeatability of the coating procedure.

Testing of Nanoelectrode

As previously reported by Lowe et al. (2003), the inventors also observed photocurrents when the gold nanoparticle-coated microelectrode was illuminated with a 100 mW 532 nm green laser with 0.1 M phosphate buffer having 0.05 M EDTA as the electrolyte. (Lowe, L. B., Brewer, S. H., Krmer, S., Fuierer, R. R., Qian, G., Agbasi-Porter, C. O., Moses, S., Franzen, S., and Feldheim, D. L. (2003). Laser-induced temperature jump electrochemistry on gold nanoparticle-coated electrodes. *Journal of the American Chemical Society*, 125(47):14258-14259). FIG. 11 shows measured photocurrents. When there were no nanoparticles coated on the microelectrode, no photocurrent was observed as shown in FIG. 11.

Similar photocurrent jumps were observed when an extracellular solution having a composition of 140 mM NaCl, 5 mM KCl, 1 mM $MgCl_2$, 2 mM $CaCl_2$, 10 mM HEPES at pH 7.4 maintained with NaOH was used as the electrolyte instead of phosphate buffer. FIG. 12 shows the measured photocurrent when the extracellular solution was used as the electrolyte. The control experiment was done with the micropipette not coated with gold nanoparticles. As shown in FIG. 12, plasmonic heating produces a temperature rise in the surrounding medium. This allows the inventors to ensure that the nanoelectrodes are sufficient to be used for plasmonic stimulation experiments with biological cells.

Plasmonic Temperature Measurements

Figure 13:
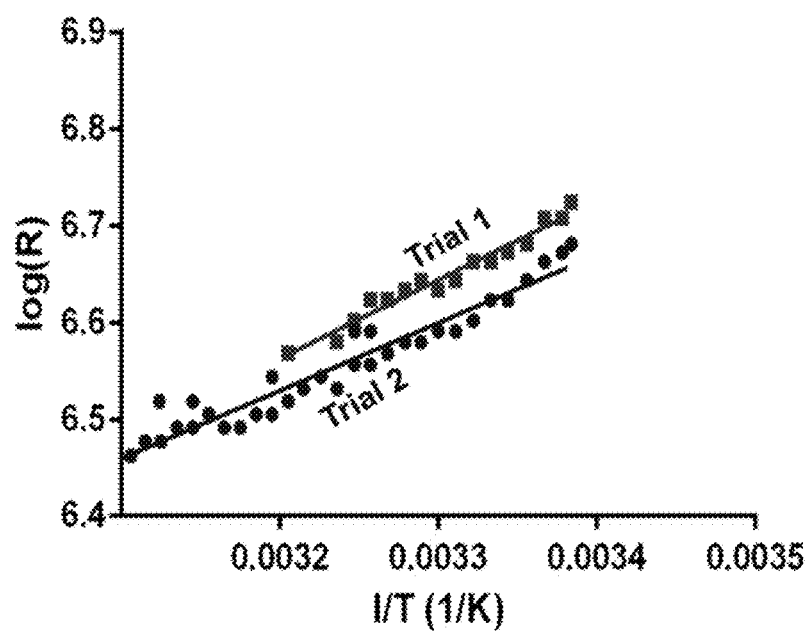
FIG. 13 is an image depicting the micropipette resistance versus temperature calibration curve. The figure shows data from two trials. The data points and line are used for temperature calculations because it has more data points.

The extracellular solution was heated to approximately 55° C., then, allowed to cool down to room temperature. The resistance of a patch pipette filled with the same extracellular solution was recorded as temperature cooled down. FIG. 13 represents the log (R) vs 1/temperature, fitted as a straight line, calibration curve.

Figure 14:
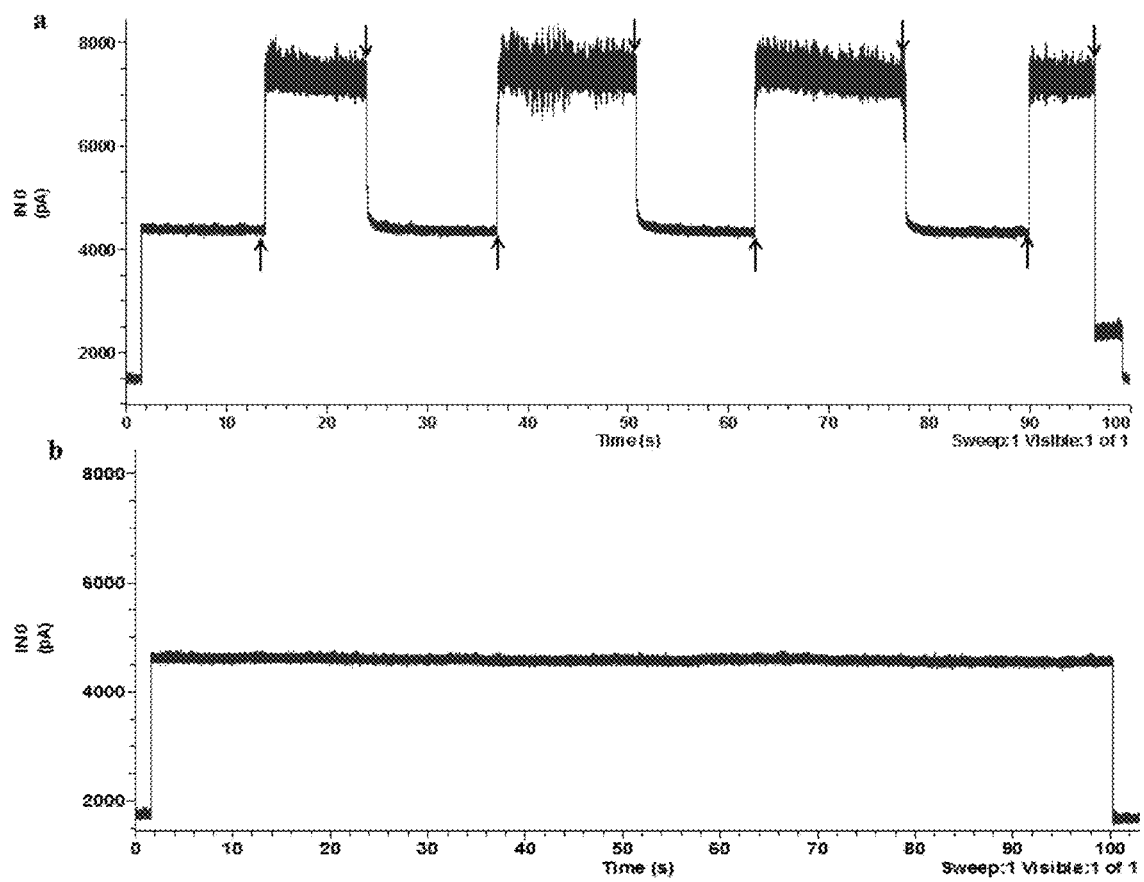
FIG. 14A-B is a series of images depicting current vs. time curves in response to a 20 mV electrical pulse; (a) when the Au nanoelectrode was present, instant jumps in current were observed as soon as the laser (100 mW, 532 nm green laser) was turned on (upward arrows). These jumps are due to plasmonic heating and correspond to a 33° C. temperature rise from room temperature to approximately 55° C. (b) There were no jumps when the nanoelectrode was not there. Downward arrows designate when the laser was turned off.

FIG. 14 shows the plasmonic temperature measurement setup where a patch pipette was placed just next to the nanoelectrode and a change in pipette resistance was measured when the laser was shone on the tip of the nanoelectrode. When 20 mV voltage pulses were applied to the patch pipette, there were extra instant jumps in current responses along on top of the voltage pulse response, as soon as the laser was turned on at maximum power (100 mW). These jumps go away when the laser was turned off (FIG. 14). There were no current jumps, when the nanoelectrode was not present (FIG. 14). These current jumps correspond to 33° C. temperature rise from the room temperature (22° C. to 55° C.). These results quantify the plasmonic heating phenomenon.

Figure 15:
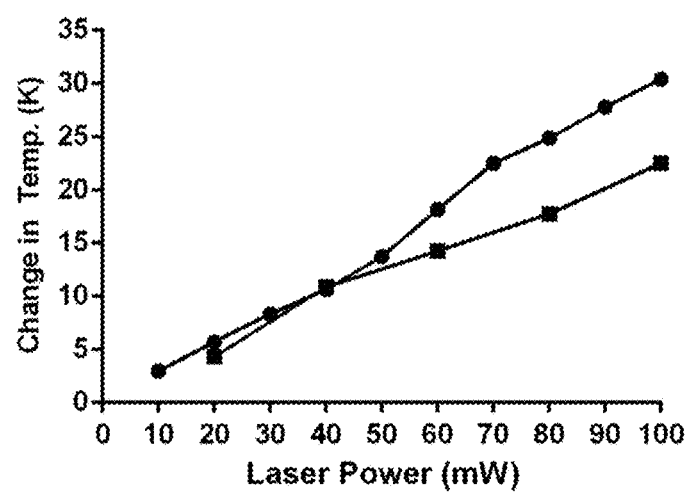
FIG. 15 is a graph depicting laser power vs. plasmonic temperature rise (Two trials). As laser power increases, temperature-rise also increased, approximately linearly.

As a control measurement, the temperature rise was studied as a function of laser power. As laser power increases, temperature also increases (FIG. 15) approximately linearly. This Figure establishes a relationship between the intensity of the light source and temperature rise (heating).

Plasmonic Physiological Responses

Figure 16:
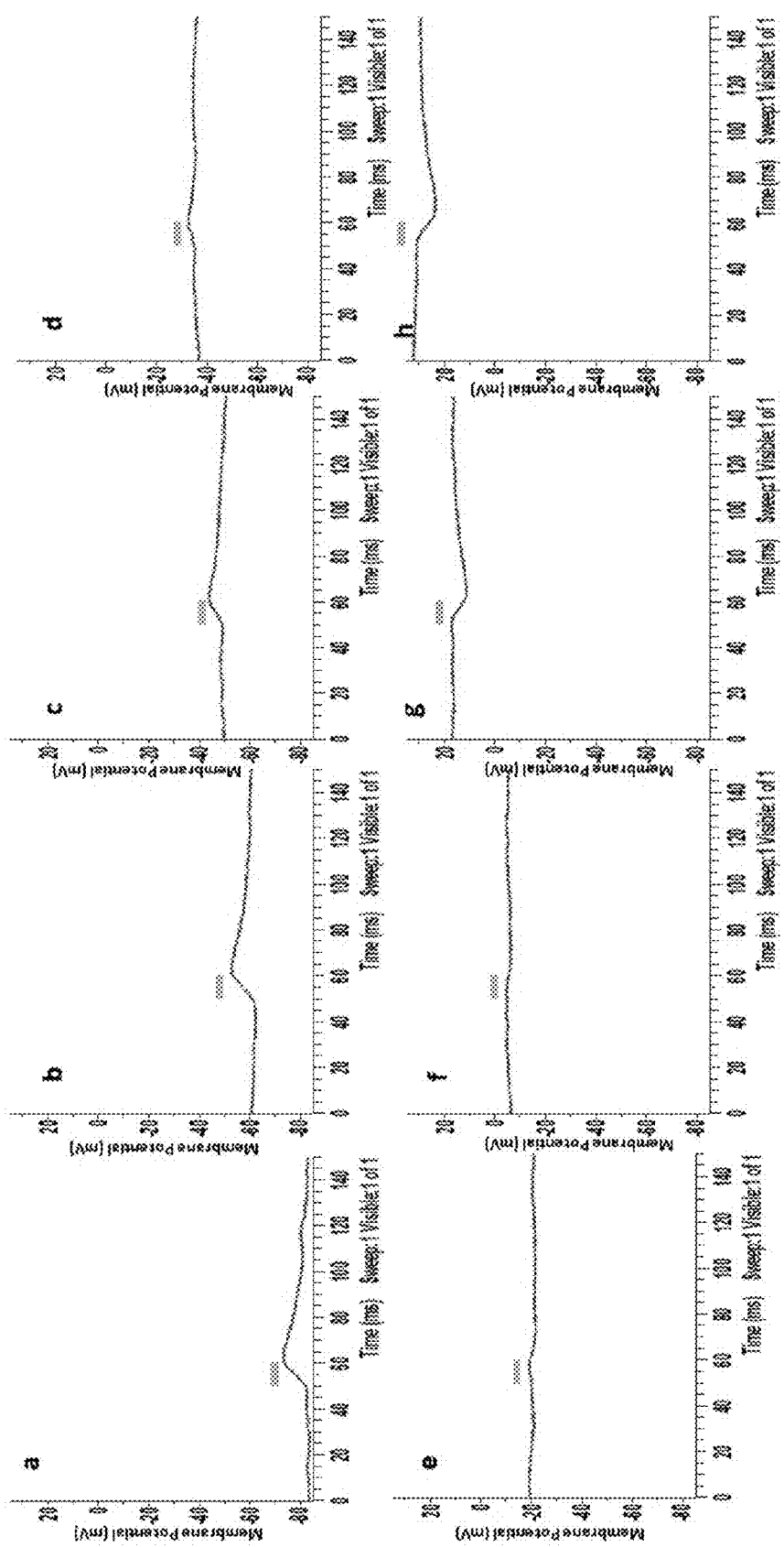
FIG. 16A-H is a series of images depicting the change in cell potential (plasmonic jumps) at different holding potentials during plasmonic stimulation, i.e. a 10 ms pulse having a power of 100 mW, was shined onto the nanoelectrode; (a) −82.4 mV holding potential, (b) −60.9 mV holding potential, (c) −48.5 mV holding potential, (d) −35.2 mV holding potential. (e) −20.1 mV resting potential, (f) −6.2 mV holding potential, (g) 17 mV holding potential, (h) 31.0 mV holding potential. The green bar represents the laser pulse timing.

All of the plasmonic stimulation experiments were done by using the patch clamp set up (FIGS. 3, 5). When SH-SY5Y cells were stimulated with a 10 ms or longer laser pulse, jumps in membrane potential (plasmonic jumps) were observed. These jumps in potential change magnitude, relative to the holding potential of the cell, were positive when the cell was at holding potentials −30 mV or less. As the holding potential approaches zero, the magnitude of the plasmonic jumps decreased and become negative as the holding potential went to more positive. FIG. 16 shows one of the recordings from a differentiated SH-SY5Y cell. Cells were firing action potential both, before and after, the plasmonic stimulation portion of the experiment.

Figure 17:
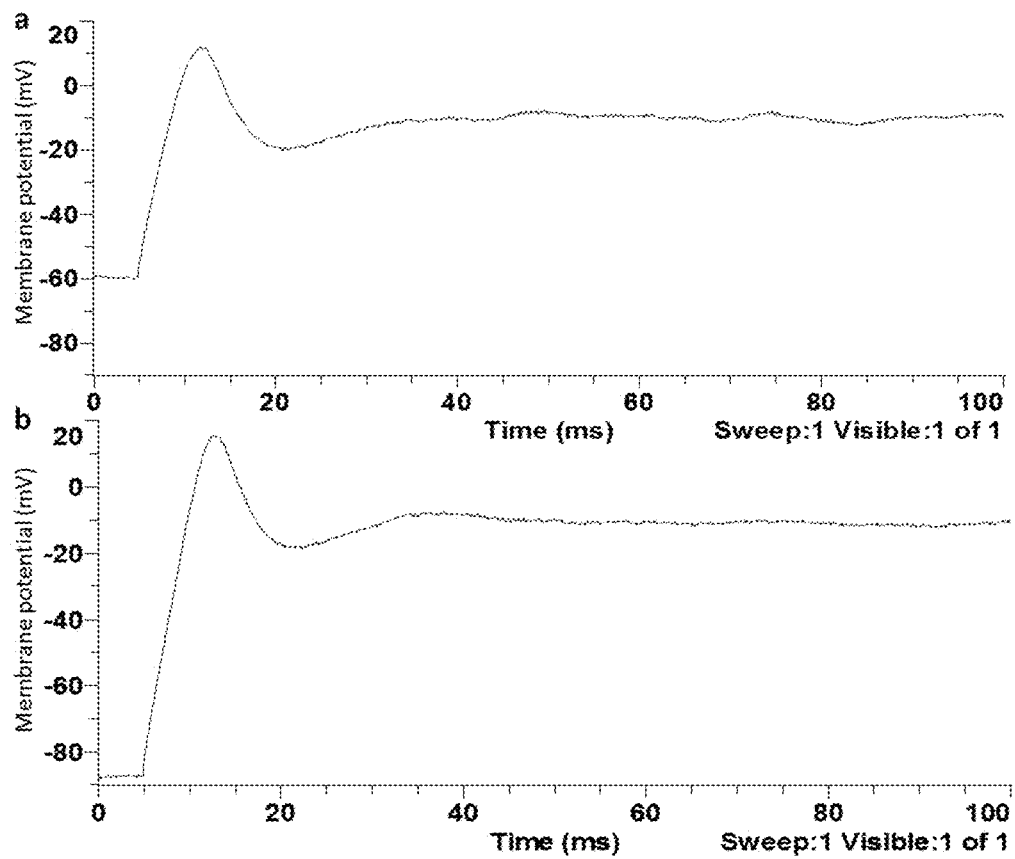
FIG. 17A-B is a series of images depicting action potentials recorded using standard whole cell current clamp procedure; (a) before the plasmonic stimulation and (b) after plasmonic stimulation. It indicates that plasmonic stimulation is not doing any thermal damage to the cell, so, the neuron is otherwise healthy.
Figure 18:
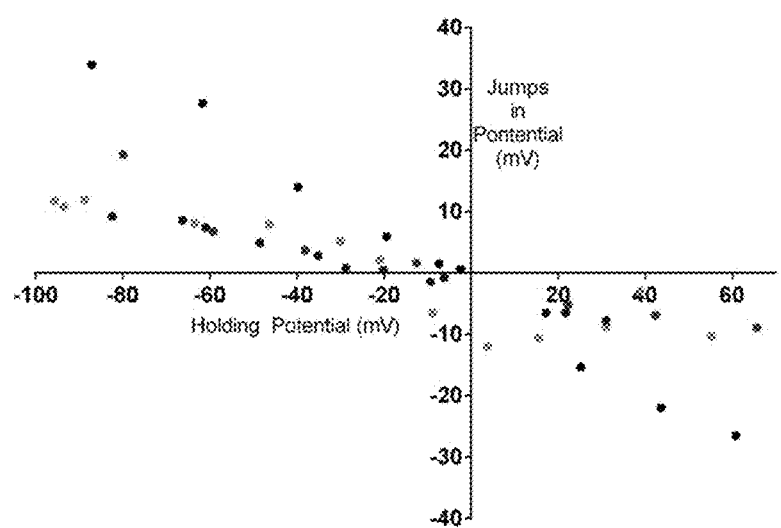
FIG. 18 is a graph depicting plasmonic jumps vs holding potential for four different neural cells (each cell is represented by different color data points). All show the same trend i.e. as holding potential goes from negative to positive, plasmonic jumps go from positive to negative.

Positive plasmonic jumps indicate the depolarization due to opening of sodium channels and negative plasmonic jumps indicate the repolarization because of the opening of potassium channels. Further experiments by applying sodium and potassium channel blockers are performed for further confirmation. FIG. 17 shows the action potential recordings before and after the plasmonic stimulation from the same cell whose plasmonic jumps are shown in FIG. 16. FIG. 18 provides the data showing the relations between plasmonic jumps and the holding potential for four different neurons. It has also been observed that magnitude of plasmonic jumps increases as laser power increases but plasmonic jumps rise at a slow rate as laser power increases. The Figures demonstrate that plasmonic stimulation can activate electrically excitable biological cells and thus has potential to be used in implants such as a cochlear implant.

Figure 19:
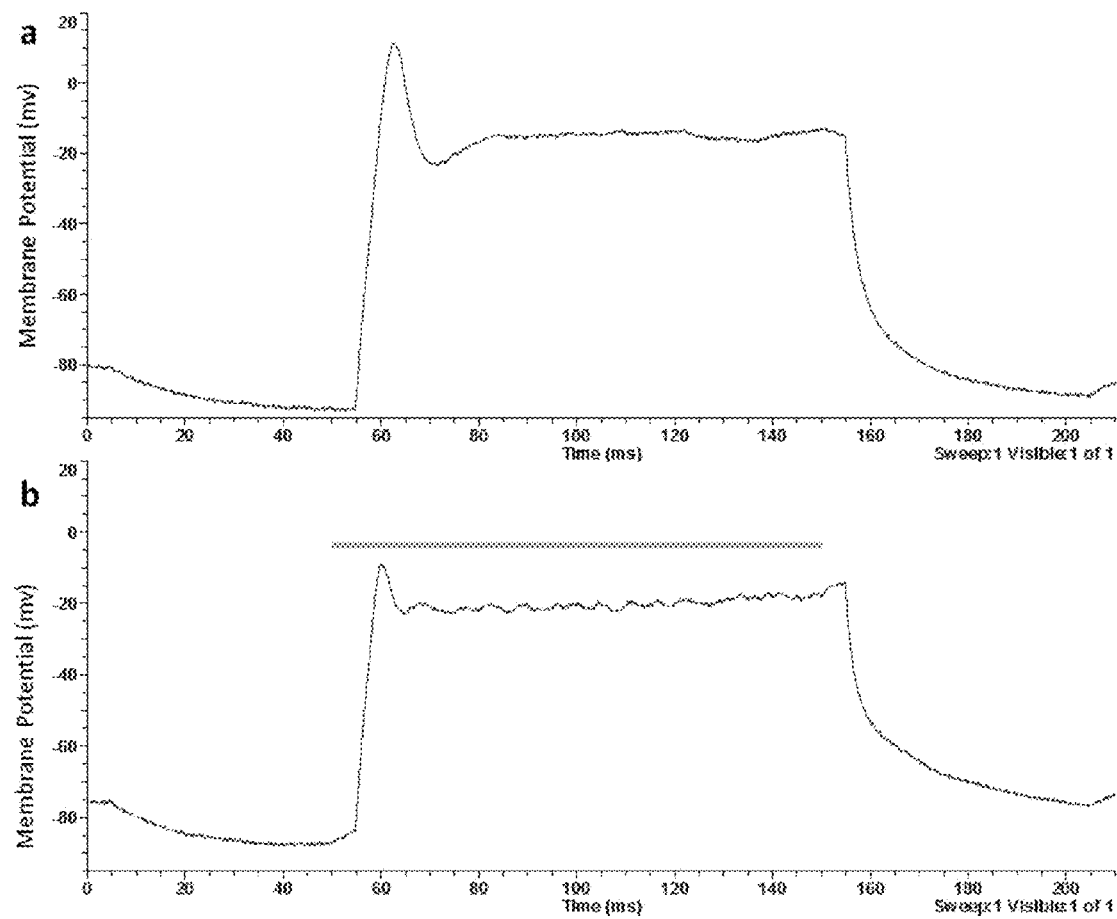
FIG. 19A-B are a series of graphs depicting decreases in the magnitude of the action potentials when a laser pulse of plasmonic stimulation was superimposed on an electrical pulse stimulus in a whole cell current clamp experiment. (a) Action potential recorded in a whole-cell current clamp experiment, (b) Action potential recorded when a 100 mW laser pulse was superimposed on the current pulse from the same neuron. The green bar indicates the laser pulse timing.

When plasmonic stimulation was superimposed on the current pulse and used to record the action potential in standard current clamp experiments, a decrease in magnitude of the action potential was observed as shown in FIG. 19.

Figure 20:
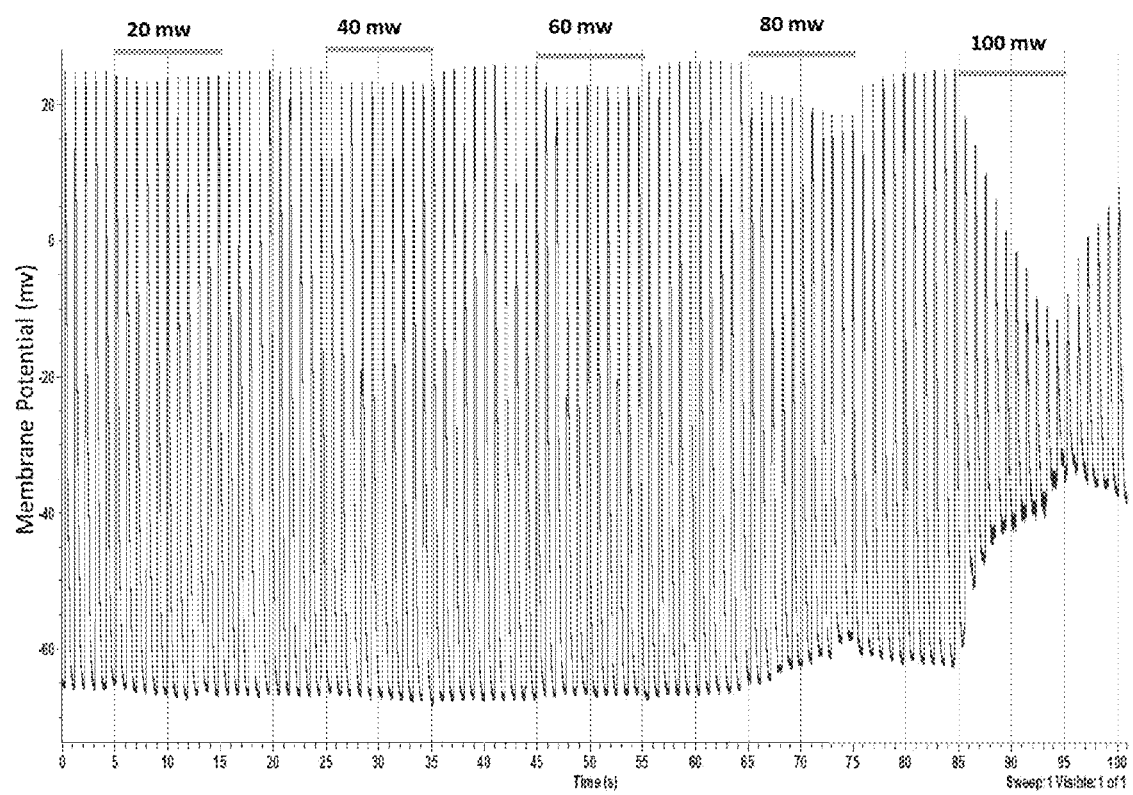
FIG. 20 is an image depicting plasmonic stimulation of spontaneous beating cardiomyocytes. Green bars shows the laser. As laser power increases, suppression in magnitude of the action potential becomes more prominent as shown in the figure, with a maximum for the 100 mW laser power.
Figure 21:
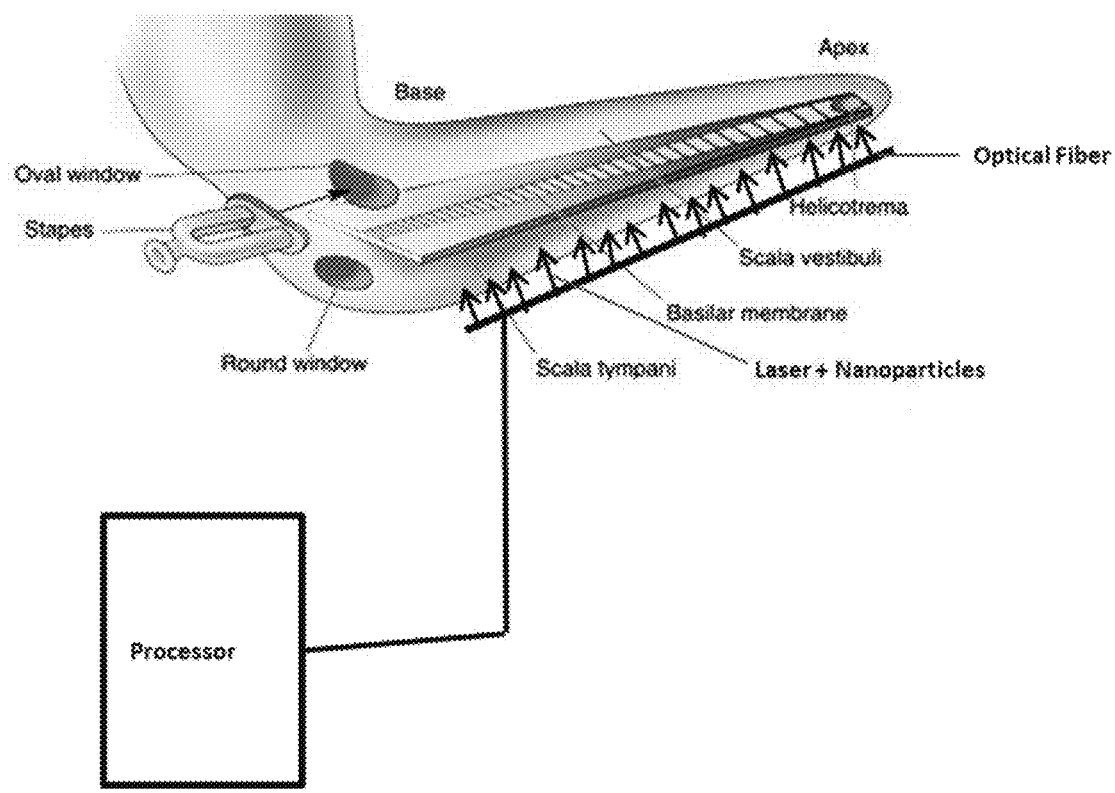
FIG. 21 is a prototype image of a cochlear implant.

Similar plasmonic jumps were also observed for neonatal cardiomyocytes (data not shown). A decrease in magnitude of action potential magnitude was seen for spontaneously beating cardiomyocytes, with decreases in magnitude becoming more prominent at higher laser power levels, as shown in FIG. 20.

Figure 22:
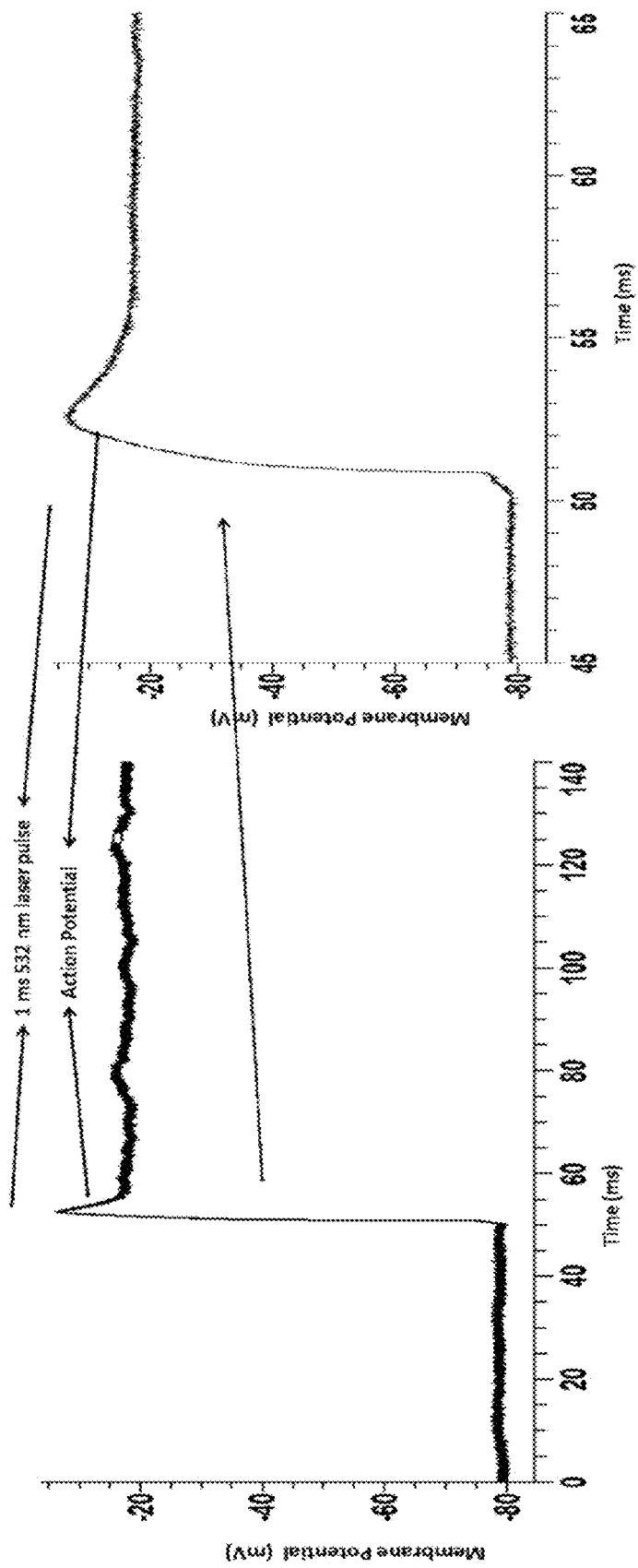
FIG. 22 is a series of graphs illustrating the action potential recorded from an SH-SY5Y neural cell when a 1 ms 532 nm green laser pulse was shone on the nanoelectrode coated with gold particles.

As shown in FIG. 22, the inventors found that for 1-5 ms laser pulses, action potentials can be initiated in SH-Sy5Y neural cells in vitro. These results provide a basis of stimulating neurons in different parts of the body, as well as heart cells and other muscle cells, with controlled laser stimulation with translational implications for better neural stimulation and diagnostic devices and clinical systems.

Yoo et al. (2014) reported inhibition in neural activity of Sprague Dawley hippocampal tissue slices when stimulated with gold nanorods and a 785 nm near IR laser. (Yoo, S., Hong, S., Choi, Y., Park, J.-H., and Nam, Y. (2014). Photothermal inhibition of neural activity with near-infrared-sensitive nanotransducers. *ACS Nano*, 8(8):8040-8049). The inventors have observed a similar inhibition of neural activity in the plasmonic stimulation experiments (FIGS. 19 and 20). Eom et al. (2014) showed neural activity enhancement utilizing infrared stimulation for rat sciatic nerve when the nerve was stimulated in the presence of gold nanorods, as compared to the controlled condition (no gold nanorods). (Eom, K., Kim, J., Choi, J. M., Kang, T., Chang, J. W., Byun, K. M., Jun, S. B., and Kim, S. J. (2014). Enhanced infrared neural stimulation using localized surface plasmon resonance of gold nanorods. *Small*, 10(19):3853-3857). However, a full action potential has not been reported in in vitro experiments using infrared light.

In these two situations, compared to the instant invention, the big difference is the laser pulse timing. In cases of neural excitatory activation in previous studies, the pulse width was sub-milliseconds, and for inhibition, the laser was on for longer time periods (seconds). Both studies referenced above used infrared stimulation which employs pulses lasting sub-milliseconds for activation and seconds for inhibition. In the current invention, visible wavelength light is used in which pulses of a few milliseconds, as opposed to sub-milliseconds, are used for activation and pulses of about 300 ms, as opposed to seconds, are used for inhibition. It seems that rate of rise in temperature is more important than the absolute temperature rise to initiate action potential in the cells. Similar results regarding absolute temperature, and temperature changes stimulated with infrared stimulation have been reported. (Wells, J., Kao, C., Konrad, P., Milner, T., Kim, J., Mahadevan-Jansen, A., and Jansen, E. D. (2007). Biophysical mechanisms of transient optical stimulation of peripheral nerve. *Biophysical journal*, 93(7):2567-2580; Duke, A. R., Jenkins, M. W., Lu, H., McManus, J. M., Chiel, H. J., and Jansen, E. D. (2013). Transient and selective suppression of neural activity with infrared light. *Scienific reports*, 3)

The use of visible wavelength light ensures that there will not be thermal damage to the cells, which can occur when using infrared stimulation. Plasmonic stimulation works on the principle of SPR peaks which are tunable according to the material properties of the nanoparticles, such as size and shape, thus allowing for increased control over the stimulation. This control allows for multiple lights and material (size/shape) to be used for implants.

The inventors identify the type of channels that are activated during the plasmonic stimulation by applying ion channel-selective blockers and determine the laser parameters that are most effective for the cells to fire action potentials. For visible wavelength light, a laser pulse width of about 1-5 ms is important for cells to fire an action potential.

After understanding plasmonic stimulation in-vitro experiments, the inventors focus on its in vivo applications, specially, on cochlear implants and peripheral neuropathy as initial applications of this breakthrough technology through the stimulation of peripheral nerves and stimulation of the auditory nerve in rodent and other animal models.

Figure 25:
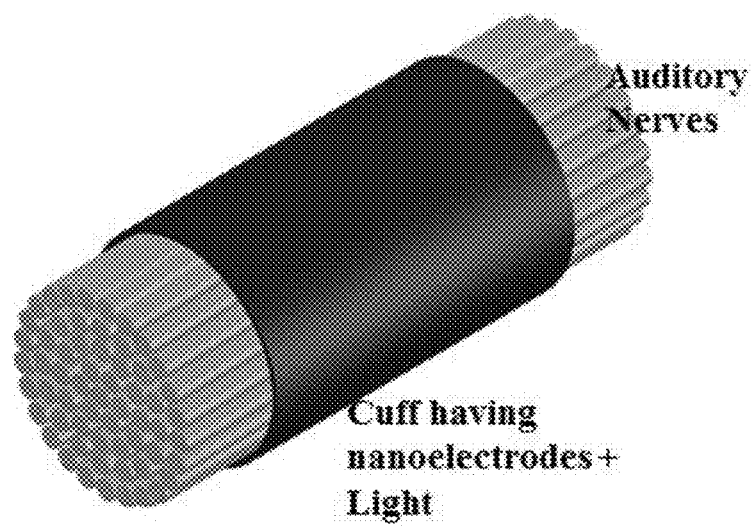
FIG. 25 is an image depicting a neural cuff in which many nanoelectrodes can be used for stimulation of frequency specific auditory nerve fibers.

Cochlear implants generally are comprised of an exterior and an interior portion. The exterior portion of the device includes a microphone, a speech processor and a transmitter while the interior portion of the device generally includes a receiver, electrical circuitry for delivering an electrical signal and an array of electrodes which receives the electrical signals and stimulates auditory fibers to perceive sound sensations. In use, the microphone collects sounds from the patient's environment and sends the sounds to the speech processor which analyzes, digitizes and sends the sound signals to the transmitter. The transmitter then sends the coded signals to the receiver which delivers the electrical signal to the electrodes to stimulate the auditory nerve fibers. The technology described herein can replace the electrical circuitry of the device so that a laser is used as an energy source to generate pulses of visible wavelength light which is then focused on a nanoelectrode through the use of an optical fiber. The light pulses activate the nanoelectrode which in turn plasmonically stimulates the auditory fibers thus allowing the sound sensations to be perceived by the patient. The alternative way of using plasmonic stimulation is to have a neural cuff around the auditory nerves. As shown in FIG. 25, the neural cuff can have nanoelectrodes and laser light source as well. The laser pulse will be focused on the nanoelectrodes which will stimulate the auditory nerves without the need for an optical fiber.

Pacemakers generally comprise three main components: a pulse generator; one or more leads; and electrodes positioned at the end of each of the leads. The pulse generator generally consists of a sealed lithium battery and an electronic circuitry package. The pulse generator is the component that produces the electrical signals that constitute a heartbeat. A pulse generator has the capability to receive and respond to signals sent by the heart itself. The leads are generally insulated flexible wires that conduct electrical signals to the heart from the pulse generator and vice versa. The technology described herein can be used in the pulse generator to conduct electrical pulses. A nanoelectrode would replace the normal electrode at the end of the lead. The leads would be replaced by optical fibers which serve to focus the light pulse from the laser on the nanoelectrode. The nanoelectrode would then in turn stimulate the cardiomyocytes.

In retinal implants, the natural optical stimulus is replaced by pulsed, light-dependent electrical stimuli which results in the perception of phosphenes. The electrical signal is triggered at the point of brightness and the stimulation strength corresponds to the intensity of the incident light so that the optical image is replaced by an electrical pattern of excitation. In general, a retinal implant contains electrical circuitry contained on a silicon chip to transmit electrical signals to an electrode which in turn stimulates retinal cells. The silicon chip can be placed on a circuit board that can transmit power and control signals. The technology described herein can be used to replace the current electrical circuitry to plasmonically stimulate the cells. The electrode is replaced with the nanoelectrode as described herein with a laser being used for the energy source. As described herein, the laser emits pulses of visible wavelength light through an optical fiber to focus the pulses of light on the nanoelectrode. The nanoelectrode receiving the pulses of light in turn stimulates the retinal cells.

Plasmomyography can use the described plasmonic stimulation technology to replace electromyography. In electromyography, electrical signals from the muscles of a patient are evaluated. In general, a small needle electrode is inserted into different muscles to stimulate the muscle fibers and electrical activity is measured when the muscle contracts and relaxes. Similarly to what has been described above, the technology described herein can replace the electrode used to stimulate the patient's muscles with a nanoelectrode which receives visible light pulses from a laser emitting light pulses in visible wavelengths. An optical fiber can be used to specifically focus the light pulses on the nanoelectrode which in turn plasmonically stimulates the muscle fibers.

CONCLUSIONS

The inventors found that plasmonic stimulation can stimulate electrically excitable biological cells which involve interaction of gold nanoparticles and other metal nanoparticles using the visible light. Plasmonic stimulation is highly localized and thus does not spread widely unlike electrical stimulation. As such, plasmonic stimulation has the potential for improved spatial resolution fidelity. Because it uses visible light, unlike infrared stimulation, the surrounding tissue does not increase in temperature. Another advantage is that as a wireless technology, there is no requirement for a wire between the nanoparticles and the light source.

In light of the foregoing advantages, plasmonic stimulation can revolutionize the existing field of biomedical implants. Potential applications include, but are not limited to, cochlear stimulation for cochlear implants; cardiac stimulation for cardiac pacemakers; muscle and nerve testing for the peripheral nerve system, e.g. plasmomyography as an alternative to electromyographs; and retinal stimulation for retinal implants.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of stimulating or inhibiting an action potential in an electrically active biological cell, the method comprising:
   placing a nanoelectrode within 0 to 6 μm of the electrically active biological cell, wherein the nanoelectrode is coated with a model-predicted array of gold nanoparticles that are configured to produce plasmonic heating sufficient to stimulate or inhibit an action potential in the electrically active biological cell but not ablate the electrically active biological cell when excited by a wavelength of light near their surface plasmon resonance peak; and
   delivering a first pulse of light on the nanoelectrode to excite the gold nanoparticles, wherein the light has a wavelength ranging from about 400 nm to about 800 nm, and wherein the wavelength of light is near the surface plasmon resonance peak of the gold nanoparticles.

2. The method of claim 1, wherein the duration of first pulse ranges from 1 to 10 ms.

3. The method of claim 1, wherein the duration of the first pulse ranges from 1 to 5 ms.

4. The method of claim 3, wherein the electrically active biological cell is an auditory nerve cell.

5. The method of claim 1, wherein the wavelength of light ranges from about 495 to about 570 nm.

6. The method of claim 1, wherein the wavelength of light is about 532 nm.

7. The method of claim 1, wherein the electrically active biological cell is a nerve cell, a cardiomyocyte, a non-cardiac muscle cell, or a retinal cell.

8. The method of claim 1, wherein the first pulse of light is delivered via a laser.

9. The method of claim 1, further comprising providing a second pulse of light on the nanoelectrode to excite the gold nanoparticles, wherein the second pulse of light is delivered after the first pulse of light, wherein there is a period of no pulse of light between the end of the first pulse of light and the beginning of the second pulse of light, and wherein the period of no pulse of light ranges between 50 and 100 ms.

10. The method of claim 9, wherein the duration of the second pulse of light ranges from 1 to 10 ms.

11. The method of claim 9, wherein the duration of the second pulse of light ranges from 1 to 5 ms.

12. The method of claim 9, wherein the duration of the first pulse of light ranges from 1 to 10 ms.

13. The method of claim 9, wherein the duration of the first pulse of light ranges from 1 to 5 ms.

14. The method of claim 9, wherein electrically active biological cell is a nerve cell, a cardiomyocyte, a non-cardiac muscle cell, or a retinal cell.

15. The method of claim 1, wherein the gold nanoparticles are about 20 nm in diameter.

16. The method of claim 1, further comprising the step of delivering an electrical pulse to the electrically active biological cell at least at the same time as delivering the first pulse of light.

17. A method of stimulating an action potential in an electrically active biologic cell, the method comprising:
   placing a nanoelectrode within 0 to 6 μm of the electrically active biological cell, wherein the nanoelectrode is coated with a model-predicted array of gold nanoparticles that are configured to produce plasmonic heating sufficient to stimulate an action potential in the electrically active biological cell but not ablate the electrically active biological cell when excited by a wavelength of light near their surface plasmon resonance peak; and
   delivering a first pulse of visible light on the nanoelectrode to excite the gold nanoparticles, wherein the visible light is near the surface plasmon resonance peak of the gold nanoparticles,
   wherein the electrically active biological cell is cell is a nerve cell, a cardiomyocyte, a non-cardiac muscle cell, or a retinal cell.

18. The method of claim 17, wherein the nanoelectrode is placed within about 2 μm of the electrically active biological cell, the visible light has a wavelength ranging from about 495 nm to about 570 nm, wherein the first pulse of the visible light is about 1 to 5 ms, and wherein the electrically active biological cell is an auditory nerve cell.

19. The method of claim 17, further comprising providing a second pulse of light ranging from about 1 to about 5 seconds on the nanoelectrode to excite the gold nanoparticles, wherein the second pulse of light is delivered after the first pulse of light, wherein there is a period of no pulse of light between the end of the first pulse of light and the beginning of the second pulse of light, and wherein the period of no pulse of light ranges between 50 and 100 ms.

20. The method of claim 17, wherein the gold nanoparticles are about 20 nm in diameter, wherein the visible light is delivered via a laser and wherein the power of the laser is 100 mW.

* * * * *